United States Patent
Levy et al.

(10) Patent No.: US 9,888,913 B2
(45) Date of Patent: *Feb. 13, 2018

(54) VARIABLE DEPTH SURGICAL FIXATION

(71) Applicant: Via Surgical Ltd., Moshav Amirim (IL)

(72) Inventors: Arie Levy, Ramat-Gan (IL); Ofek Levin, Moshav Amirim (IL); Lena Levin, Moshav Amirim (IL)

(73) Assignee: Via Surgical Ltd., Moshav Amirim (IL)

( * ) Notice: Subject to any disclaimer, the term of this patent is extended or adjusted under 35 U.S.C. 154(b) by 293 days.

This patent is subject to a terminal disclaimer.

(21) Appl. No.: 13/768,726

(22) Filed: Feb. 15, 2013

(65) Prior Publication Data

US 2014/0058417 A1   Feb. 27, 2014

Related U.S. Application Data

(63) Continuation-in-part of application No. 13/523,500, filed on Jun. 14, 2012, now Pat. No. 8,535,339.
(Continued)

(51) Int. Cl.
*A61B 17/04* (2006.01)
*A61F 2/00* (2006.01)
(Continued)

(52) U.S. Cl.
CPC ...... *A61B 17/0469* (2013.01); *A61B 17/0401* (2013.01); *A61B 17/064* (2013.01);
(Continued)

(58) Field of Classification Search
CPC ..... A61B 17/128; A61B 17/10; A61B 17/105; A61B 17/0482; A61B 17/0483;
(Continued)

(56) References Cited

U.S. PATENT DOCUMENTS 2,881,762 A   4/1959  Lowrie
3,212,502 A   10/1965 Myers
(Continued)

FOREIGN PATENT DOCUMENTS

CN    101507626 A   8/2009
CN    101969859 A   2/2011
(Continued)

OTHER PUBLICATIONS

International Search Report and Written Opinion dated Oct. 29, 2013 for International Application Serial No. PCT/IB2013/000647, filed Feb. 15, 2013 (17 pages).
(Continued)

*Primary Examiner* — Christopher L Templeton
(74) *Attorney, Agent, or Firm* — Brown Rudnick LLP; Thomas C. Meyers

(57) ABSTRACT

The invention generally relates to devices for fastening a hernia mesh. The invention provides a surgical fastening device that includes a shaft with a fastener carrier disposed at least partially within the shaft, in which the carrier is configured to accept fasteners of a plurality of different sizes. Different sized fasteners can be preloaded in interchangeable carriers or even mixed together within a carrier in the fastening device. The device can deliver the fasteners to different depths in a patient's tissue.

13 Claims, 39 Drawing Sheets

Related U.S. Application Data

(60) Provisional application No. 61/653,792, filed on May 31, 2012.

(51) Int. Cl.
*A61B 17/00* (2006.01)
*A61B 17/06* (2006.01)
*A61B 17/064* (2006.01)
*A61B 17/29* (2006.01)

(52) U.S. Cl.
CPC ........ *A61F 2/0063* (2013.01); *A61B 17/0482* (2013.01); *A61B 17/0483* (2013.01); *A61B 2017/00309* (2013.01); *A61B 2017/00323* (2013.01); *A61B 2017/0409* (2013.01); *A61B 2017/0417* (2013.01); *A61B 2017/0472* (2013.01); *A61B 2017/0477* (2013.01); *A61B 2017/0488* (2013.01); *A61B 2017/06042* (2013.01); *A61B 2017/0647* (2013.01); *A61B 2017/0648* (2013.01); *A61B 2017/0649* (2013.01); *A61B 2017/06052* (2013.01); *A61B 2017/06176* (2013.01); *A61B 2017/2923* (2013.01)

(58) Field of Classification Search
CPC ............ A61B 17/04; A61B 2017/0488; A61B 2017/0472; A61B 2017/07235; A61B 2017/07242; A61B 17/0682; A61B 17/068; A61B 2017/0725; A61B 2017/047
See application file for complete search history.

(56) References Cited

U.S. PATENT DOCUMENTS

| | | | |
|---|---|---|---|
| 4,069,825 A | 1/1978 | Akiyama | |
| 4,235,238 A | 11/1980 | Ogiu et al. | |
| 4,391,402 A | 7/1983 | Campbell et al. | |
| 4,394,864 A | 7/1983 | Sandhaus | |
| 4,458,835 A | 7/1984 | Li et al. | |
| 4,536,933 A | 8/1985 | Furutsu | |
| 4,809,695 A | 3/1989 | Gwathmey et al. | |
| 4,900,303 A | 2/1990 | Lemelson | |
| 4,950,285 A | 8/1990 | Wilk | |
| 5,037,433 A | 8/1991 | Wilk et al. | |
| 5,123,913 A | 6/1992 | Wilk et al. | |
| 5,174,487 A | 12/1992 | Rothfuss et al. | |
| 5,222,961 A | 6/1993 | Nakao et al. | |
| 5,242,457 A | 9/1993 | Akopov et al. | |
| 5,290,310 A | 3/1994 | Makower et al. | |
| 5,330,488 A | 7/1994 | Goldrath | |
| 5,356,064 A | 10/1994 | Green et al. | |
| 5,364,002 A | 11/1994 | Green et al. | |
| 5,364,022 A | 11/1994 | Ganz | |
| 5,392,978 A | 2/1995 | Velez et al. | |
| 5,425,489 A | 6/1995 | Shichman et al. | |
| 5,431,676 A * | 7/1995 | Dubrul ............... | A61B 17/3439 604/164.1 |
| 5,445,167 A | 8/1995 | Yoon et al. | |
| 5,582,616 A | 12/1996 | Bolduc et al. | |
| 5,626,587 A | 5/1997 | Bishop et al. | |
| 5,662,662 A * | 9/1997 | Bishop et al. ................. | 606/143 |
| 5,728,113 A | 3/1998 | Sherts | |
| 5,814,058 A * | 9/1998 | Carlson .............. | A61B 17/3439 606/185 |
| 5,827,319 A * | 10/1998 | Carlson .............. | A61B 17/3439 604/264 |
| 5,830,221 A | 11/1998 | Stein et al. | |
| 5,895,395 A | 4/1999 | Yeung | |
| 5,916,146 A | 6/1999 | Allotta et al. | |
| 5,964,394 A | 10/1999 | Robertson | |
| 5,968,044 A | 10/1999 | Nicholson et al. | |
| 6,156,039 A | 12/2000 | Thal | |
| 6,306,149 B1 | 10/2001 | Meade | |
| 6,425,900 B1 | 7/2002 | Knodel et al. | |
| 6,447,524 B1 | 9/2002 | Knodel et al. | |
| 6,494,886 B1 | 12/2002 | Wilk et al. | |
| 6,530,933 B1 | 3/2003 | Yeung et al. | |
| 6,607,542 B1 | 8/2003 | Wild | |
| 6,638,286 B1 | 10/2003 | Burbank et al. | |
| 6,733,506 B1 | 5/2004 | McDevitt et al. | |
| 7,004,970 B2 | 2/2006 | Cauthen, III et al. | |
| 7,125,413 B2 | 10/2006 | Grigoryants et al. | |
| 7,141,057 B2 | 11/2006 | Burbank et al. | |
| 7,338,502 B2 | 3/2008 | Rosenblatt | |
| 7,398,908 B2 | 7/2008 | Holsten et al. | |
| 7,431,730 B2 | 10/2008 | Viola | |
| 7,591,783 B2 | 9/2009 | Boulais et al. | |
| 7,594,923 B2 | 9/2009 | Fallin et al. | |
| 7,625,386 B2 | 12/2009 | Abe et al. | |
| 7,704,261 B2 | 4/2010 | Sakamoto et al. | |
| 7,708,180 B2 | 5/2010 | Murray et al. | |
| 7,776,066 B2 | 8/2010 | Onuki et al. | |
| 7,842,047 B2 | 11/2010 | Modesitt et al. | |
| 7,850,701 B2 | 12/2010 | Modesitt et al. | |
| 7,913,891 B2 | 3/2011 | Doll et al. | |
| 7,918,868 B2 | 4/2011 | Marshall et al. | |
| 7,959,640 B2 | 6/2011 | Kantsevoy et al. | |
| 8,034,076 B2 | 10/2011 | Criscuolo et al. | |
| 8,070,035 B2 | 12/2011 | Holsten et al. | |
| 8,075,572 B2 | 12/2011 | Stefanchik et al. | |
| 8,091,756 B2 | 1/2012 | Viola | |
| 8,114,099 B2 | 2/2012 | Shipp | |
| 8,132,705 B2 | 3/2012 | Viola et al. | |
| 8,177,795 B2 | 5/2012 | Niese et al. | |
| 8,211,126 B2 | 7/2012 | Yeh et al. | |
| 8,216,272 B2 | 7/2012 | Shipp | |
| 8,277,373 B2 | 10/2012 | Maahs et al. | |
| 8,282,670 B2 | 10/2012 | Shipp | |
| 8,343,176 B2 | 1/2013 | Criscuolo et al. | |
| 8,535,339 B2 | 9/2013 | Levin et al. | |
| 8,603,118 B2 | 12/2013 | Yeh et al. | |
| 8,814,885 B2 | 8/2014 | Domingo | |
| 8,961,530 B2 | 2/2015 | Bhatnagar et al. | |
| 2001/0046646 A1 | 11/2001 | Koba | |
| 2002/0068951 A1 * | 6/2002 | Burbank et al. .............. | 606/167 |
| 2002/0107530 A1 | 8/2002 | Sauer et al. | |
| 2003/0139752 A1 | 7/2003 | Pasricha et al. | |
| 2003/0208209 A1 | 11/2003 | Gambale et al. | |
| 2004/0098045 A1 | 5/2004 | Grafton et al. | |
| 2004/0204723 A1 | 10/2004 | Kayan | |
| 2005/0131390 A1 * | 6/2005 | Heinrich ............ | A61B 17/0469 606/1 |
| 2006/0235443 A1 | 10/2006 | Huitema et al. | |
| 2007/0045379 A1 | 3/2007 | Shelton | |
| 2007/0112361 A1 | 5/2007 | Schonholz et al. | |
| 2007/0179509 A1 | 8/2007 | Nagata et al. | |
| 2007/0250064 A1 | 10/2007 | Darois et al. | |
| 2007/0270637 A1 | 11/2007 | Takemoto et al. | |
| 2008/0091219 A1 | 4/2008 | Marshall et al. | |
| 2008/0097523 A1 | 4/2008 | Bolduc et al. | |
| 2008/0110958 A1 | 5/2008 | McKenna et al. | |
| 2008/0255591 A1 | 10/2008 | Harada et al. | |
| 2008/0314954 A1 | 12/2008 | Boudreaux | |
| 2009/0018554 A1 | 1/2009 | Thorne et al. | |
| 2009/0114233 A1 | 5/2009 | Edoga et al. | |
| 2009/0206144 A1 | 8/2009 | Doll et al. | |
| 2009/0209980 A1 | 8/2009 | Harris | |
| 2009/0222083 A1 | 9/2009 | Nguyen et al. | |
| 2009/0259251 A1 | 10/2009 | Cohen | |
| 2010/0016870 A1 | 1/2010 | Campbell | |
| 2010/0069930 A1 | 3/2010 | Roslin et al. | |
| 2010/0094248 A1 | 4/2010 | Nguyen et al. | |
| 2010/0096435 A1 | 4/2010 | Fuchs et al. | |
| 2010/0145361 A1 | 6/2010 | Francischelli et al. | |
| 2010/0160931 A1 | 6/2010 | Karpiel et al. | |
| 2010/0191283 A1 | 7/2010 | Foerster et al. | |
| 2010/0292710 A1 | 11/2010 | Daniel et al. | |
| 2010/0298774 A1 | 11/2010 | Igov | |
| 2010/0318107 A1 | 12/2010 | Mizrahy et al. | |
| 2010/0327042 A1 | 12/2010 | Amid et al. | |
| 2010/0331863 A2 | 12/2010 | Saliman et al. | |

(56) References Cited

U.S. PATENT DOCUMENTS

| | | |
|---|---|---|
| 2011/0071548 A1* | 3/2011 | Yeh et al. ............... 606/144 |
| 2011/0092992 A1 | 4/2011 | Darois et al. |
| 2011/0098728 A1 | 4/2011 | McDevitt et al. |
| 2011/0118757 A1 | 5/2011 | Pierce |
| 2011/0130774 A1 | 6/2011 | Criscuolo et al. |
| 2011/0178534 A1 | 7/2011 | Whitman et al. |
| 2011/0319932 A1 | 12/2011 | Avelar et al. |
| 2012/0016389 A1 | 1/2012 | Kantsevoy et al. |
| 2012/0089157 A1 | 4/2012 | Forsell |
| 2012/0097731 A1 | 4/2012 | Knodel et al. |
| 2012/0109132 A1 | 5/2012 | Ellis et al. |
| 2012/0116424 A1 | 5/2012 | Lee et al. |
| 2012/0193394 A1 | 8/2012 | Holcomb et al. |
| 2012/0245629 A1 | 9/2012 | Gross et al. |
| 2012/0248171 A1 | 10/2012 | Bailly et al. |
| 2012/0265218 A1 | 10/2012 | Chen et al. |
| 2012/0310259 A1 | 12/2012 | Sorrentino et al. |
| 2012/0330354 A1 | 12/2012 | Kane et al. |
| 2012/0330356 A1* | 12/2012 | Rosenberg ............... 606/232 |
| 2013/0012961 A1 | 1/2013 | Reeser |
| 2013/0018394 A1 | 1/2013 | Gambale |
| 2013/0186936 A1 | 7/2013 | Shelton, IV |
| 2013/0317524 A1 | 11/2013 | Grigoryants et al. |
| 2015/0272566 A1 | 10/2015 | Arai et al. |

FOREIGN PATENT DOCUMENTS

| | | |
|---|---|---|
| EP | 1206924 A1 | 5/2002 |
| EP | 1721575 A2 | 11/2006 |
| EP | 1759812 A1 | 3/2007 |
| JP | 5-161655 A | 6/1993 |
| WO | 96/03925 A1 | 2/1996 |
| WO | 2007/139785 A2 | 12/2007 |
| WO | 2009/100242 A2 | 8/2009 |
| WO | 2010/084424 A1 | 7/2010 |
| WO | 2011/068533 A1 | 6/2011 |

OTHER PUBLICATIONS

International Search Report and Written Opinion in related international application PCT/IB12/02957 dated Jun. 20, 2013 (10 pages).

Abhishek, et al., 2012, Laparoscopic Umbilical Hernia Repair: Technique Paper, ISRN Minimally Invasive Surgery, pp. 1-4, Article ID 906405.

Nguyen, et al., 2008, Postoperative Pain After Laparoscopic Ventral Hernia Repair: a Prospective Comparison of Clips Versus Tacks, JSLS 12:113-116.

Web page <http://www.lsisolutions.com/rd180deviceanatomy> accessed on Mar. 29, 2012 (1 page).

Web page <http://www.covidien.com/silsstitch/pages.aspx> accessed on Mar. 29, 2012 (2 pages).

Gillian, et al., 2002, Laparoscopic Incisional and Ventral Hernia Repair (LIVH): An Evolving Outpatient Technique, JSLS 6(4):315-322.

Extended European search report dated Apr. 22, 2015, for European patent application 12859826.5, which application is a regional stage entry of International Patent Application PCT/IB2012/002957, filed Dec. 17, 2012 (5 pages).

* cited by examiner

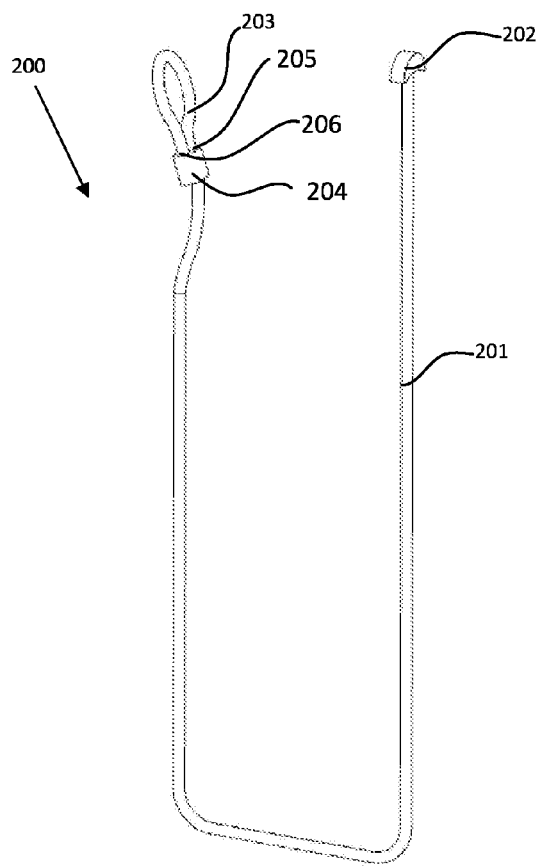
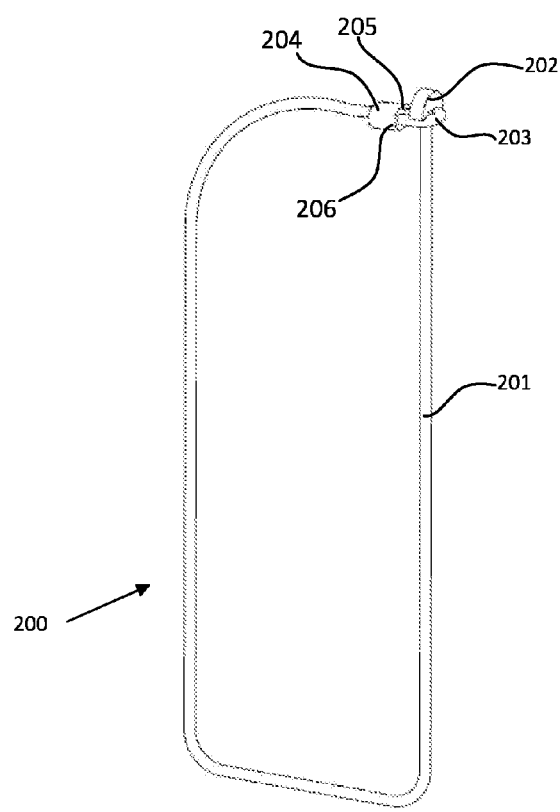
Fig 2A
Fig 2B

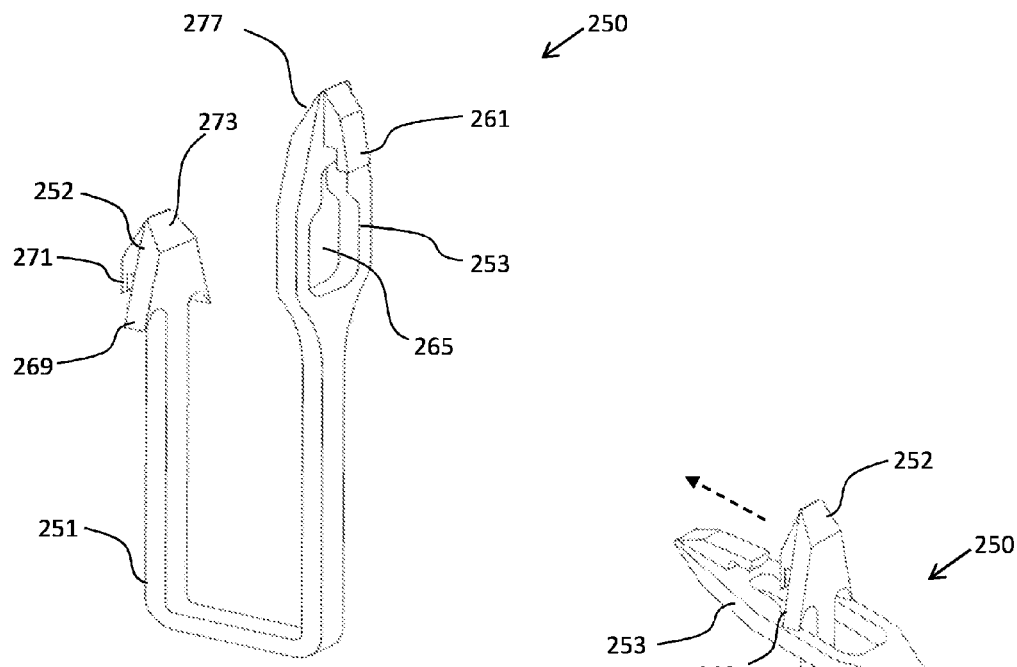
Fig 7A
Fig 7B
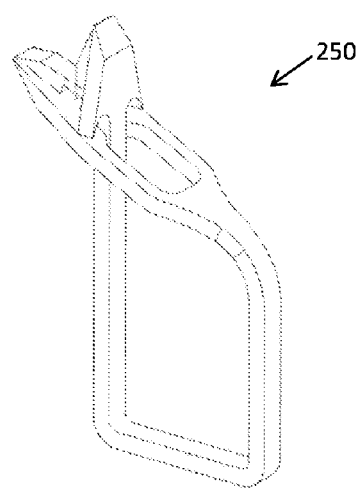
Fig 7C

VARIABLE DEPTH SURGICAL FIXATION

CROSS-REFERENCE TO RELATED APPLICATION

This application is a continuation-in-part of U.S. patent application Ser. No. 13/523,500, filed Jun. 14, 2012, and claims priority to U.S. Provisional Application No. 61/653,792, filed on May 31, 2012, the contents of each of which are hereby incorporated by reference in their entirety.

FIELD OF THE INVENTION

The invention generally relates to clips, surgical tacks, sutures, and fasteners, delivery devices, and methods of use thereof particularly as it relates to hernia mesh fixation.

BACKGROUND

If a person has a hernia, they may suffer from pain, organ dysfunction, bowel obstruction, or other complications. This occurs when an organ protrudes through the wall that normally contains it. Hernias can occur in a number of parts of the body, and occur commonly in the abdomen. For example, the peritoneum that lines the abdomen may push out through a weakened area of the abdominal wall to form a small balloon-like sac. This can allow a loop of intestine or abdominal tissue to push into the sac.

One method of hernia repair involves using a surgical procedure known as laparoscopy to cover the hernia with a prosthetic mesh and fix it in place with fasteners. The fasteners are typically either sutures or specialized tacks that are delivered by a fastening device configured to reach into the abdominal cavity through an incision.

A surgeon makes a small incision in the skin and inserts surgical implements as well as a laparoscope—a small telescope with a camera attached. The surgeon uses the laparoscope to study the hernia and surrounding tissue of the abdominal wall. Naturally, the thickness of the layers of the abdominal wall varies from person to person and even from place to place within a patient. For example, the layers of fat may be thick or thin depending on a person's physical fitness. Unfortunately, there is no established method or device that allows a surgeon to fix a hernia mesh with fasteners having different penetration depths or sizes to accommodate the variation in thickness of the abdominal wall.

What is particularly problematic is that the shortcomings of current methods are associated with a risk of complications and patient pain. If the abdominal muscle wall is too thick due to obesity, the fasteners will not penetrate deeply enough, and the hernia mesh will not be fixed in place successfully. If the wall is to thin, the length of the fasteners poses a significant risk of pain and complications. Fasteners for the hernia mesh that protrude deeply into a patient's tissue exacerbate the patient's post-operative pain.

SUMMARY

The invention provides a fastening device that can be loaded with fasteners, or clips, of varying sizes, allowing a surgeon to select the right fastener without having to switch to a different fastening device. Different sized fasteners can be preloaded in interchangeable carriers or even mixed together within a carrier in a fastening device. For example, if the carrier of a fastening device is loaded with four long fasteners, four medium fasteners, and four short fasteners and a surgeon views the mesh fixation site and determines that medium-sized fasteners are needed, the surgeon can eject four fasteners outside of the patient and then insert the fastening device and perform the mesh fixation. Similarly, any number of pre-loaded cartridges can be laid out at-the-ready and, upon viewing the target site, the surgeon can select the appropriate cartridge to be loaded into the fastener. The fastening device thus minimizes the cost and complexity of surgical set up and also, by minimizing the number of different instruments that must be inserted into the patient, reduces the risk of complications such as infections. Since tools of the invention allow a surgeon to use fasteners with the best length for a particular site, fasteners can be used that are long enough to fasten the mesh securely, but not so long as to cause excessive post-operative pain. Since the mesh is fastened securely, healing progresses well and recurrence of the hernia is avoided.

In certain aspects, the invention provides a fastening device that includes a shaft with a fastener carrier disposed at least partially within the shaft, in which the carrier is configured to accept fasteners or clips of a plurality of different sizes. The fastener or clip carrier may be a replaceable or interchangeable cartridge, may be preloaded with fasteners or clips of a mixture of different sizes, or both. The proximal portion of the device may include a handle and trigger. The device may be configured so that positioning the carrier at tissue and operating the trigger delivers one fastener or clip into the tissue. Preferably, the next fastener or clip is loaded into the delivery mechanism as part of the process of delivering the one fastener or clip. The fastening device may be configured to deliver different types of hernia mesh fasteners or clips such as sutures or tacks. As used herein, fastener may be taken to include any of the clips, tacks, or clips shown or discussed. In some embodiments, the carrier is configured to accept fasteners that comprise short helical tacks and fasteners that comprise long helical tacks. One operation (e.g., squeeze) of the trigger displaces a helical tack by a fixed distance along an axis of the shaft. The inside surface of the carrier may be threaded to push the tacks forward by rotation. Operating the trigger may advance a tack from the device into tissue.

In certain embodiments, for example, where anchor-style fasteners are used, the carrier is configured to accept fasteners of different lengths, and one operation of the trigger advances a hammer by a fixed distance. An anchor-style fastener may present one or more barbed struts to penetrate the hernia mesh. The hammer is shaped to grasp one fastener.

In some embodiments, the carrier is configured to deliver the clip-style fasteners through the coordinated lateral translation of a pair of insertion needles. In certain embodiments, the carrier is configured to accept stretchable tacks.

In the embodiments disclosed herein, a surgeon need not perform any adjustment during operation to switch between different sizes of fasteners. The mechanism of the fastening device operates to properly delivery fasteners of differing lengths or sizes without requiring operator intervention between ones of differing lengths or sizes.

Additionally, the invention provides a fastening device that delivers a pre-formed clip (i.e., a fastener), to a hernia mesh from a proximal side of the mesh. The fastening device may be pre-loaded with a plurality of pre-formed clips, as represented by any of the embodiments disclosed herein. When delivered, the pre-formed clip extends through the hernia mesh to a certain depth into the tissue. The pre-formed clip is fully delivered with a single operation of the trigger to a depth that is not limited by the diameter of the device shaft (i.e., the elongated shaft extending from the handle and dimensioned to pass through standard laparoscopic equipment). In certain embodiments, the delivery depth of each pre-formed clip is represented by a physical dimension of the clip or fastener. That is, each pre-formed clip may be disposed at the applicator section of the shaft and exhibit a length that substantially represents the delivery depth and that length is not constrained by, and may be arbitrarily larger than, the shaft diameter. Delivery of the pre-formed clip includes performing a single operation of the trigger to fasten the hernia mesh by inserting the pre-formed clip to the depth while also, in the same operation of the trigger, loading the next pre-formed clip into position at the applicator section for delivery by the next single operation of the trigger. Preferably, the dimension of the clip and the delivery depth can vary from one pre-formed clip to the next and require no intervening adjustment by the operator.

In certain aspects, the invention provides a method of fastening a hernia mesh by using a fastening device with a shaft operably coupled to a handle to deliver, from a carrier operably connected to the shaft, a first fastener to tissue and using the device to deliver a second fastener, the second fastener having a different size than the first fastener.

BRIEF DESCRIPTION OF THE DRAWINGS

FIGS. 2A and 2B illustrate a clip applied by the clip applicator.

FIGS. 7A-7C show a clip according to certain embodiments.

DETAILED DESCRIPTION

The current invention provides clips, delivery devices, and methods for fastening a clip to tissue. The invention provides methods and devices for suturing by pushing two ends of a clip through tissue from a proximal side of the tissue and fastening the two ends together on a distal side of the tissue through one operation of a trigger. Clips and devices of the invention are useful for securing a prosthetic device to a tissue or for wound closure or any other medical need requiring the use of a clip.

Figure 1A:
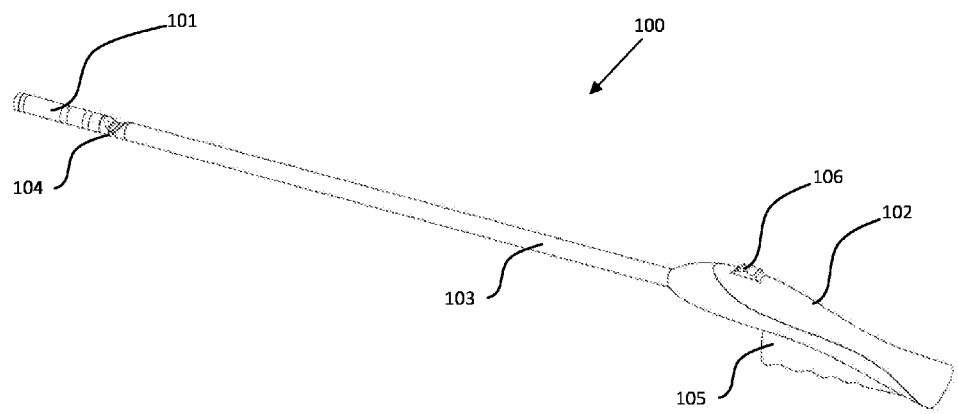
FIGS. 1A and 1B illustrate one embodiment of a clip applicator.
Figure 1B:
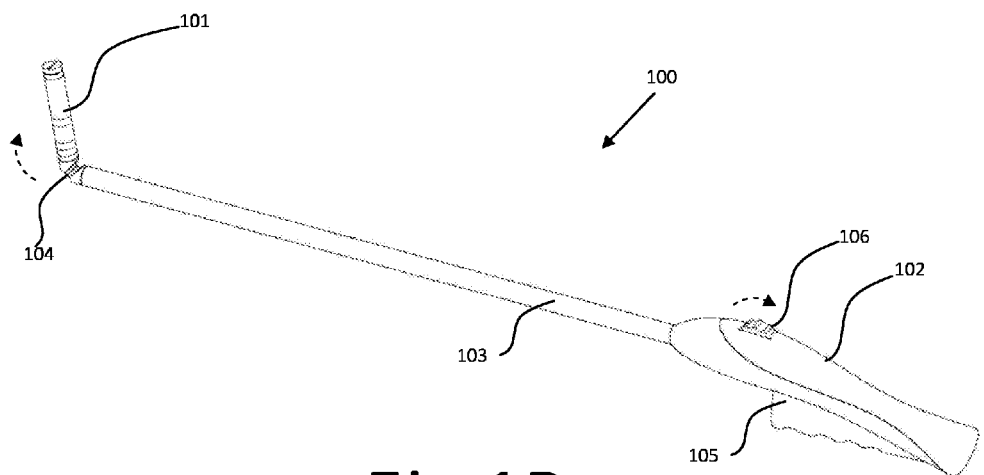

FIGS. 1A and 1B depict a fastening device 100 according to certain embodiments. Fastening device 100 is adapted to place and secure at least one clip inside a tissue during a minimal invasive surgical operation. Fastening device 100 has an applicator section 101 and a handle section 102 connected via shaft 103. Applicator section 101 is adapted to pass through an incision or standard trocar, and to make contact with, and insert a clip into, the tissue. Applicator section 101 operates as a fastener carrier by being operably connected to shaft 103 (e.g., either one can be partially disposed within the other, they can be manufactured and assembled together, etc.).

Handle section 102 allows a practitioner to control clip application. Handle section 102 includes trigger 105, which may generally include a lever mechanism. Operation of trigger 105 delivers and fastens a clip as described below.

In certain embodiments, shaft 103 is articulated around an articulation joint 104 in order to place a clip inside the tissue in a correct angle in respect to the tissue surface (FIG. 1B). Handle 102 includes articulation knob 106 adapted to control the articulation.

FIGS. 2A and 2B illustrate a clip 200 according to certain embodiments. Clip 200 includes wire 201. A hook 202 is connected to one end of wire 201 and a loop 202 is connected to the other end. Clip 200 can include monofilament, multifilament or metallic material, in addition it can be made from a biodegradable material.

Clip 200 is characterized by at least two configurations: an open configuration (FIG. 2A), in which hook 202 and loop 203 are not connected to each other therefore allowing the insertion of clip 200 into tissue; and a closed configuration (FIG. 2B) in which hook 202 is inserted through loop 203 therefore forming a closed loop and securing clip 200 to the tissue.

In certain embodiments, loop 203 has a diameter that can be decreased such that loop 203 is tightened (e.g., once hook 202 is inserted through loop 203), thus preventing unintended disengagement of hook 202 from loop 203. Tightening is accomplished by loop holder 204. Loop holder 204 includes two holes 205 and 206. Wire 201 extends through hole 205 and hole 206. The wire 201 is connected to said loop holder 204 at hole 206 (by welding gluing or any other attachment mean) while free movement of wire 201 in relation the loop holder 204 at hole 205 is allowed. Thus, once tension is applied to wire 201, loop 203 is tightened.

Additionally or alternatively, hook 202 can be expanded once it is inserted through loop 203 (e.g., while loop 203 remains static). Expansion can be provided by shaping hook 202 as an arrowhead which deforms and compresses to pass through loop 203 and then expands back to its original shape.

Figure 3A:
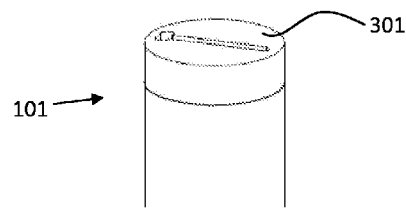
FIGS. 3A-3G illustrate various stages during application of a clip.
Figure 3B:
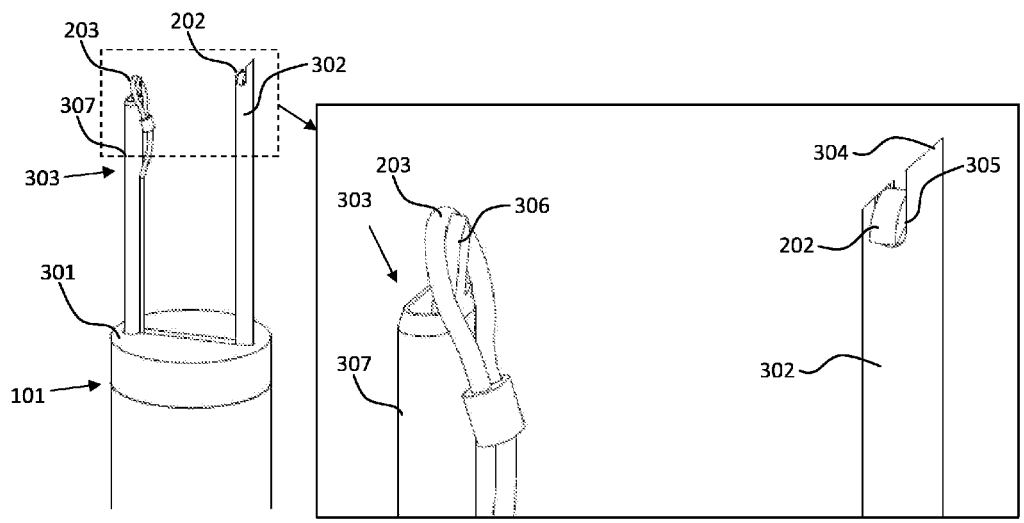

FIGS. 3A-3G illustrate a method of delivering and fastening clip 200 into tissue 300 (not shown). At the first stage (FIG. 3A), distal tip 301 of fastening device 100 is brought to the tissue surface. Next, clip 200 is inserted into the tissue by hook insertion needle 302 and loop insertion needle 303 (FIG. 3B).

Hook insertion needle 302 is adapted to insert hook 202 of clip 200 into tissue 300. In some embodiments, hook insertion needle 302 is characterized by an open cross section (e.g. "C" shaped) such that hook insertion needle 302 could be removed from clip 200 once the clip is closed. Hook insertion needle 302 is characterized by a sharp distal tip 304 adapted to penetrate through tissue 300. Distal tip 304 of hook insertion needle 302 includes two of lateral groove 305 to hold hook 202 during said insertion.

Loop insertion needle 303 is adapted to insert loop 203 into tissue 300 in curved path such that loop 203 is positioned directly above hook 202. Loop insertion needle 303 has a flexible needle 306 housed inside an insertion tube 307. Flexible needle 306 is characterized by a sharp and narrow tip adapted to penetrate the tissue while holding loop 203. The distal section of flexible needle 306 is pre-curved (see FIG. 3C). During initial insertion, flexible needle 306 is held straight inside said insertion tube 307. In certain embodiments, flexible needle 306 includes a super-elastic material such as, for example, a nickel-titanium alloy such as that sold as Nitinol by Nitinol Devices & Components, Inc. (Fremont, Calif.).

Figure 3C:
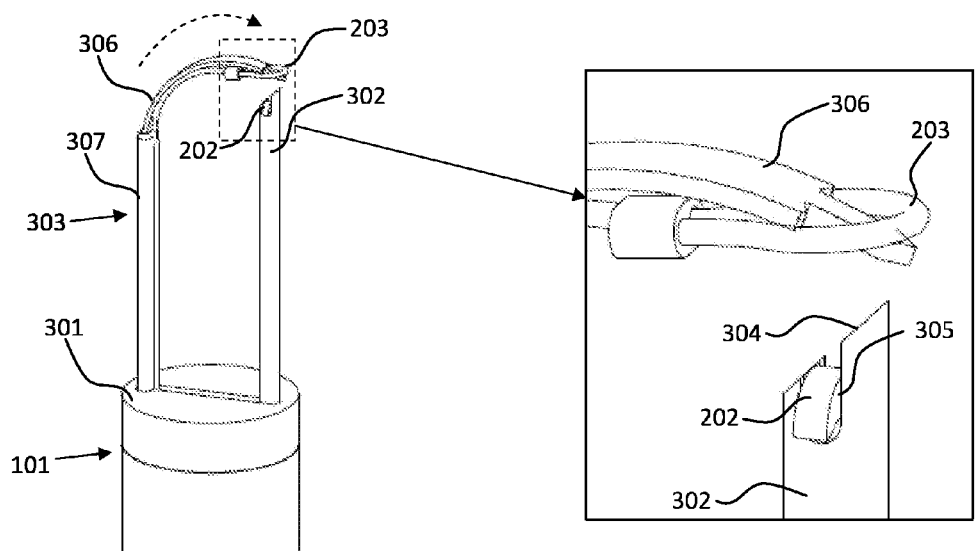
Figure 3D:
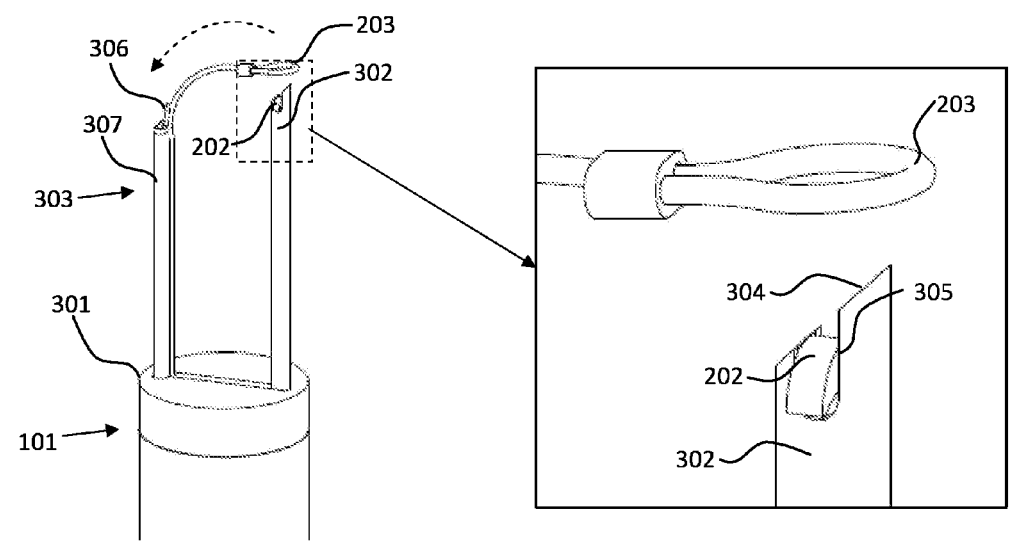
Figure 3E:
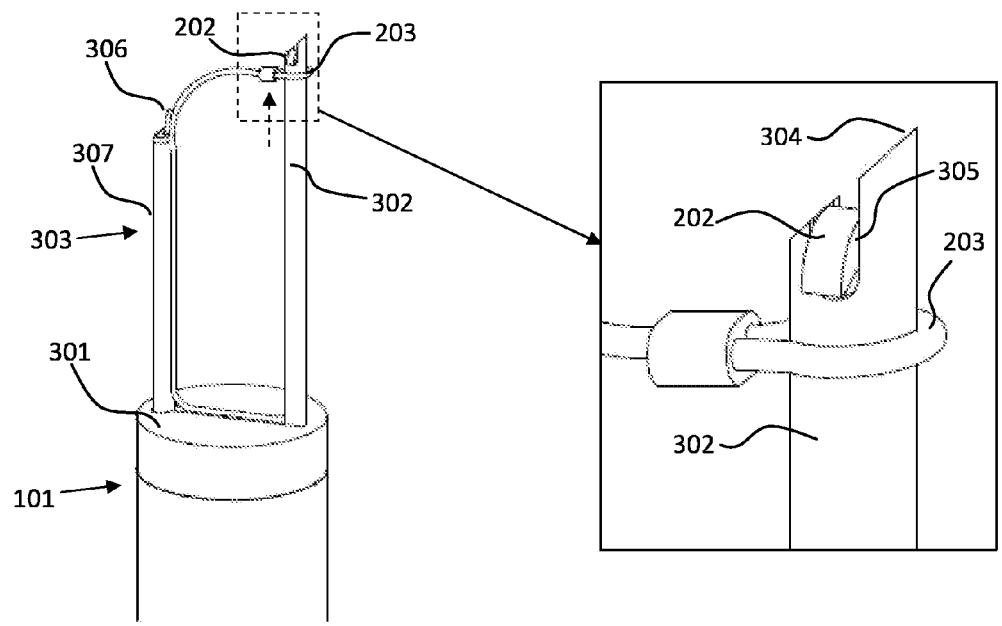
Figure 3F:
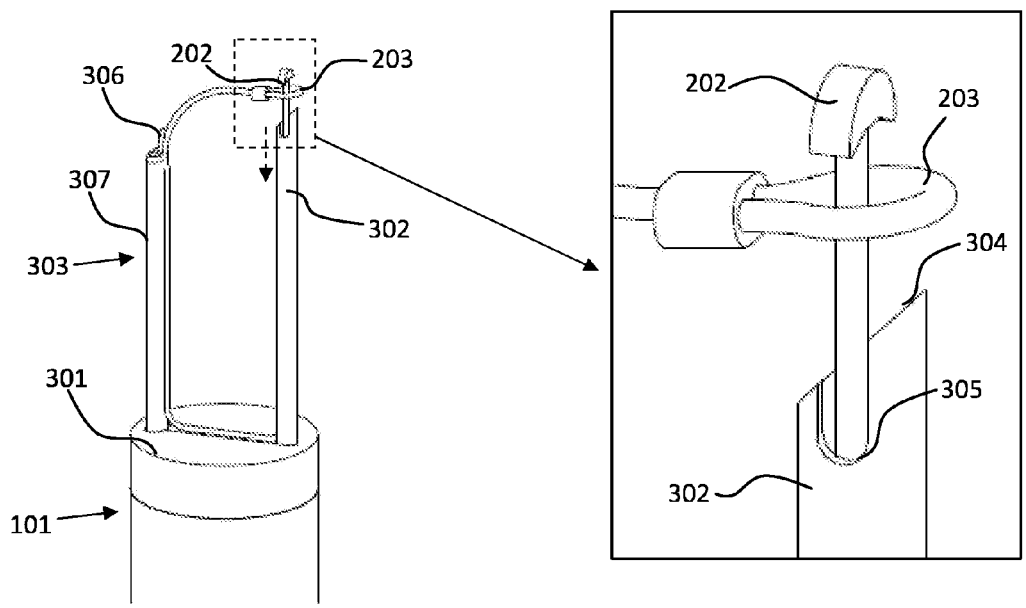
Figure 3G:
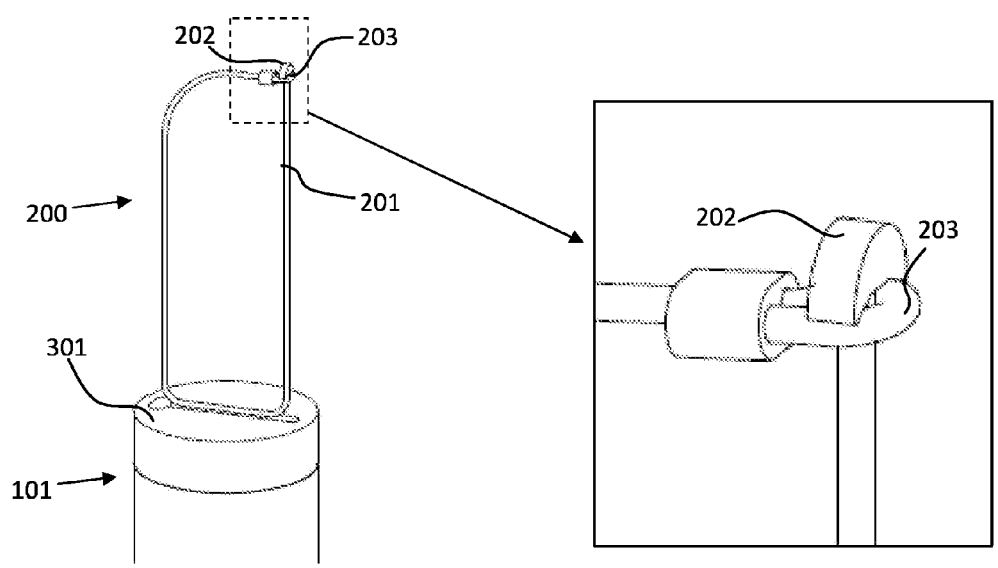

As shown in FIG. 3C, flexible needle 306 is extended out of said insertion tube 307, penetrating tissue 300 in a curved path while pulling and positioning loop 203 above hook 202 and distal tip 304 of hook insertion needle 302. Flexible needle 306 can then be retracted back into said insertion tube 307 (FIG. 3D), leaving loop 203 inside the tissue above hook 202.

At the next stage (FIG. 3E), hook insertion needle 302 is advanced further into the tissue while inserting hook 202 through loop 203. In this stage, tension is applied at clip 200, which causes loop 202 the tighten around said needle 302.

At the next stage (FIG. 3F), hook insertion needle 302 is retracted, leaving hook 202 located inside said loop 203.

At the final stage (FIG. 3G), both of hook insertion needle 302 and loop insertion needle 303 are removed from the tissue. Additional tension can be applied the clip 200, causing further tightening of loop 203 and leaving clip 200 secured inside the tissue.

In certain embodiments, a reticulation of the distal end of fastening device 100 allows the distal tip to be rotated around its longitudinal axis. This can allow the application of clips in various orientation in respect to said fastening device 100.

Reference is now made to FIGS. 4A-4D, which illustrates use of fastening device 100 for securing a hernia mesh 400 to the innermost layer of abdominal wall 401 during laparoscopic hernia repair surgery. In general, the outermost layer of the abdominal wall is the skin, followed by two layers of fibrous connective tissue (the campers fascia then the Scarpas fascia), three layers of muscle (the external oblique muscle, the internal oblique muscle, and the transverse abdominal muscle), a layer of fat (the preperitoneal fat), and then the peritoneum—a membrane that surrounds the abdominal cavity.

Figure 4A:
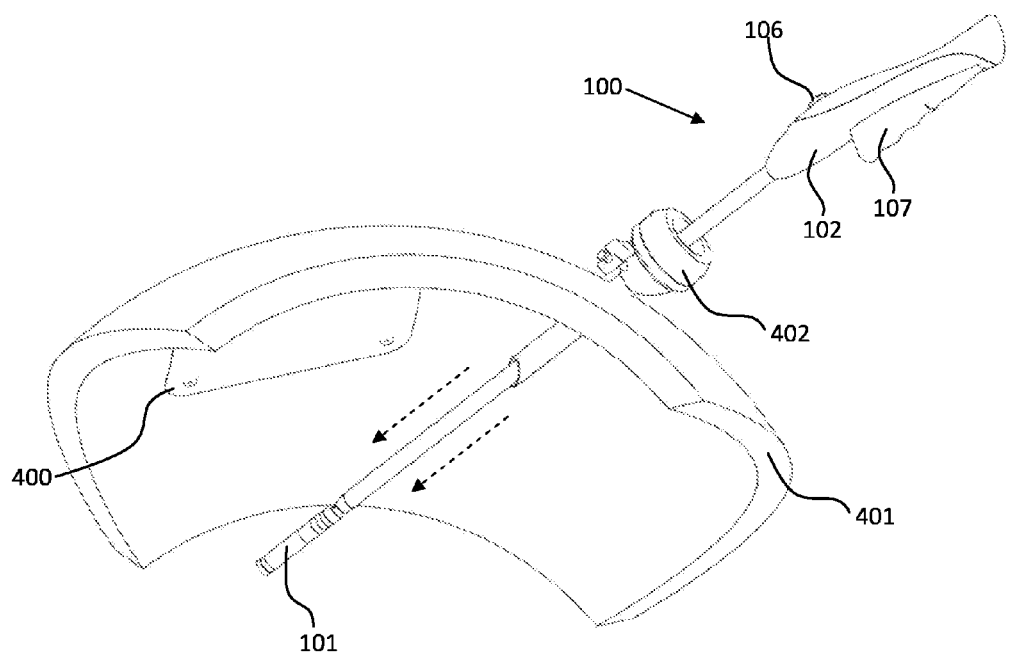
FIGS. 4A-4D illustrate fixating a hernia mesh to an abdominal wall.
Figure 4B:
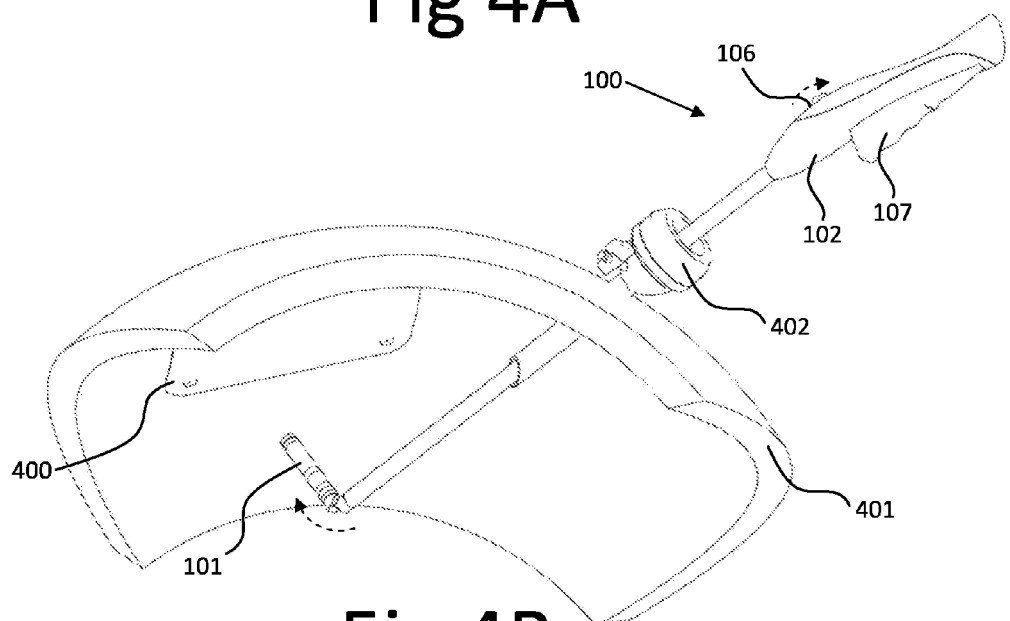
Figure 4C:
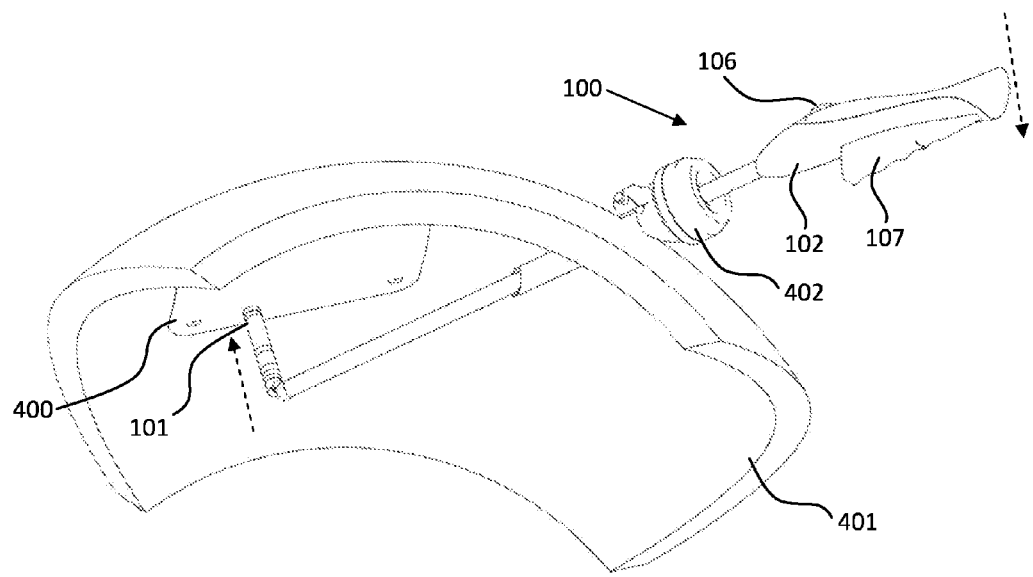
Figure 4D:
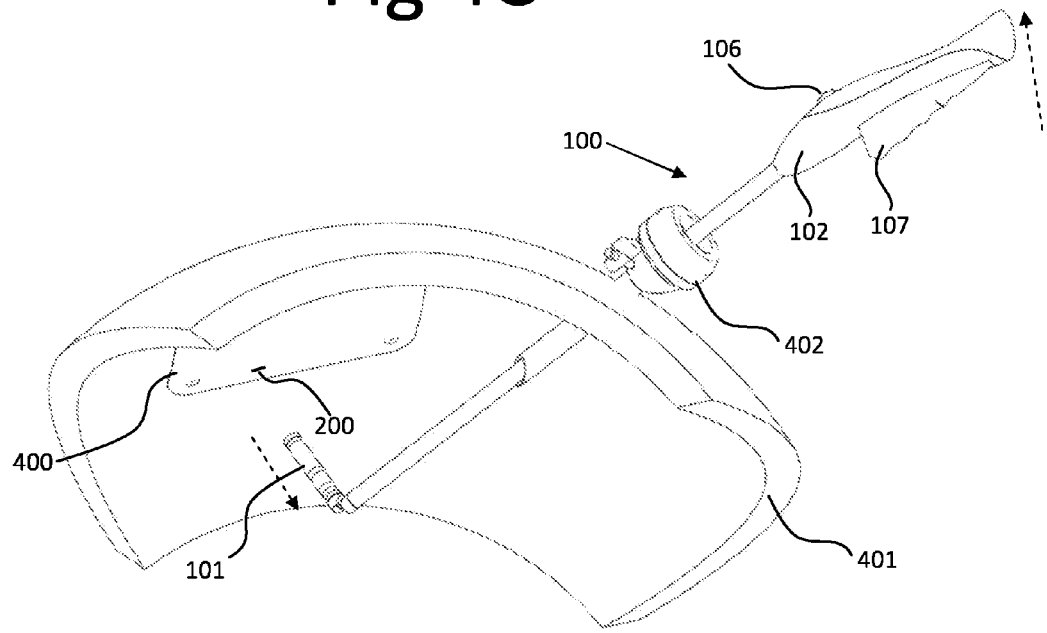

In certain aspects, the invention provides devices and methods for securing mesh 400 to tissue. Methods include inserting a distal portion of fastening device 100 into a patient's abdominal cavity through a trocar 402 or through an incision (FIG. 4A). Applicator section 101 can be articulated via articulation knob 106 (FIG. 4B). Distal tip 301 is pressed against hernia mesh 400 (FIG. 4C) and a single clip is delivered through the tissue and hernia mesh 400 and secured in place by pressing lever 107 on handle 102. Tip 301 is removed as shown in FIG. 4D.

Figure 5A:
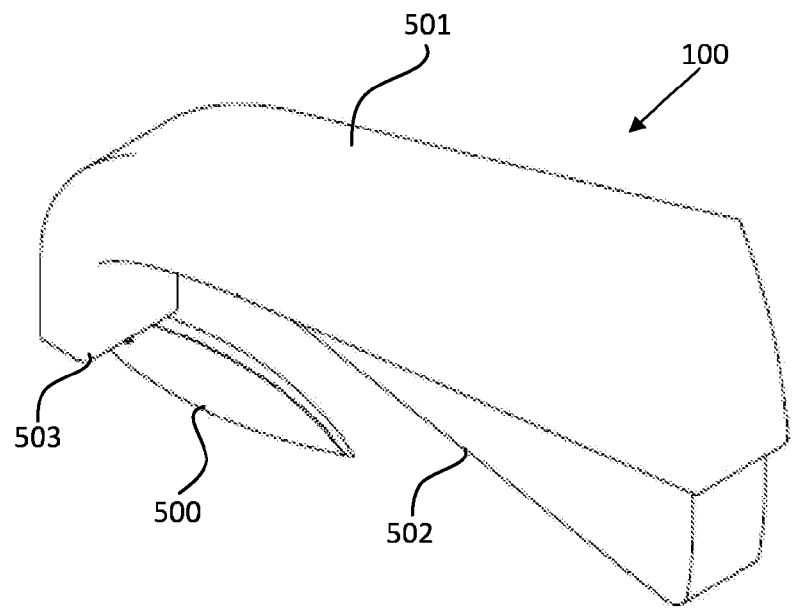
FIGS. 5A-5B illustrate use of the clip applicator for wound closure applications.
Figure 5B:
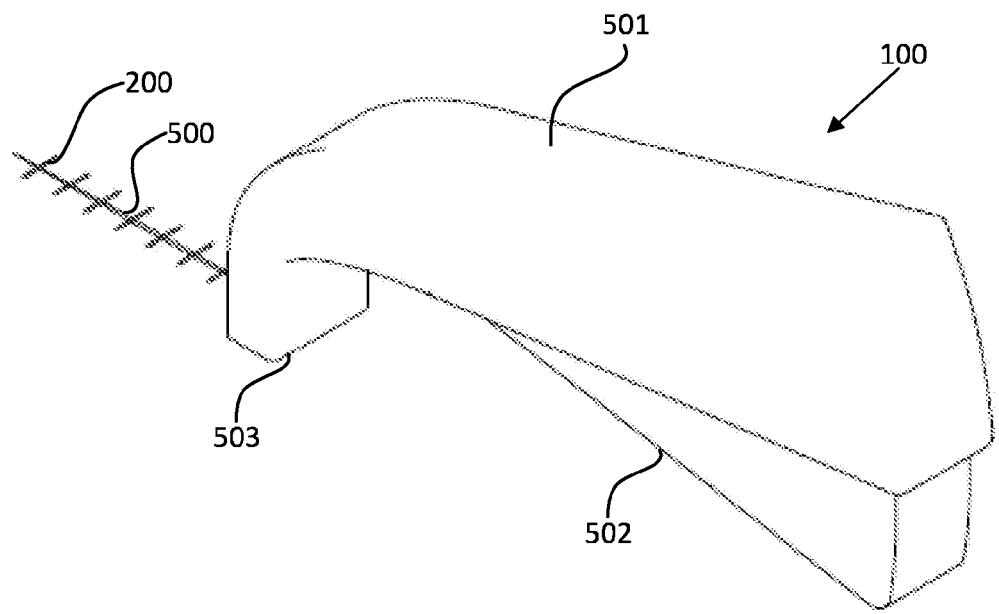

Reference is now made to FIGS. 5A-5B which show use of applicator 100 for closure of wound 500. Applicator 100 comprises a body 501 and activation lever 502 adapted to initiate clip application by the user. According to this embodiment, a wound is closed by pressing the distal tip 503 of fastening device 100 to wound 500 (FIG. 5A) and applying at least one clip 200 through both sides of said wound 500 (FIG. 5B).

FIGS. 6A-6H illustrate a mechanism of action for wound closure. The process is similar to the one shown in FIGS. 3A-3G, however it includes a step for bringing two sides of a wound together before securing clip 200 to the tissue. For illustration purposes, the tissue and the wound is not shown in these drawings.

Figure 6A:
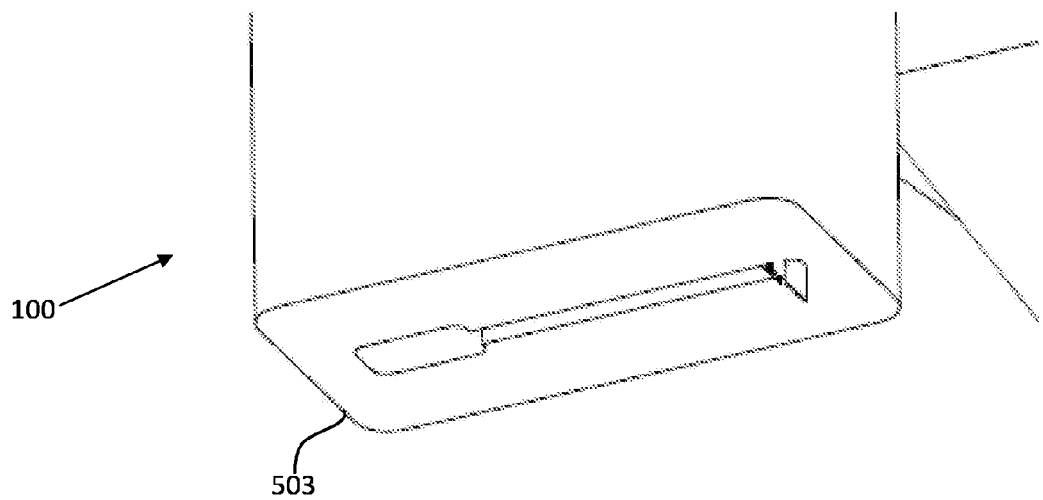
FIGS. 6A-6H illustrate application of a clip during wound closure operation.
Figure 6B:
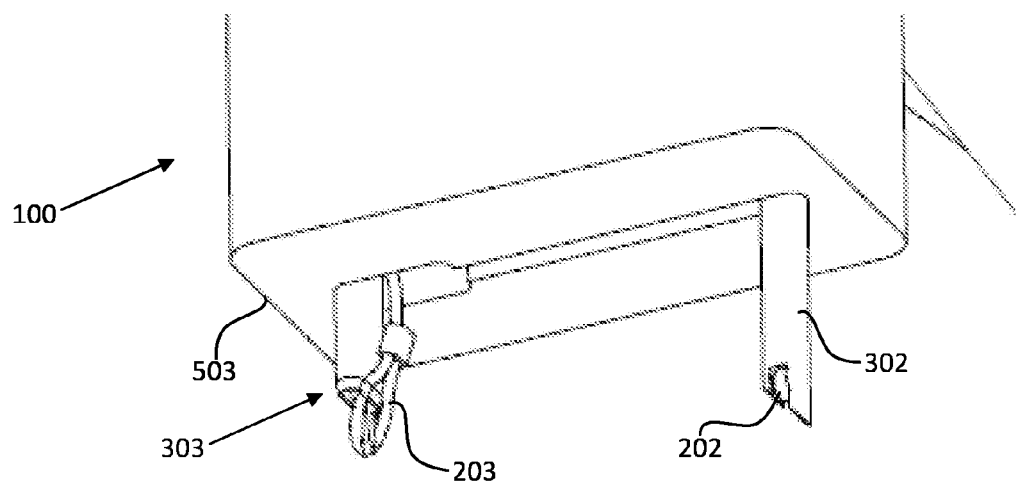
Figure 6C:
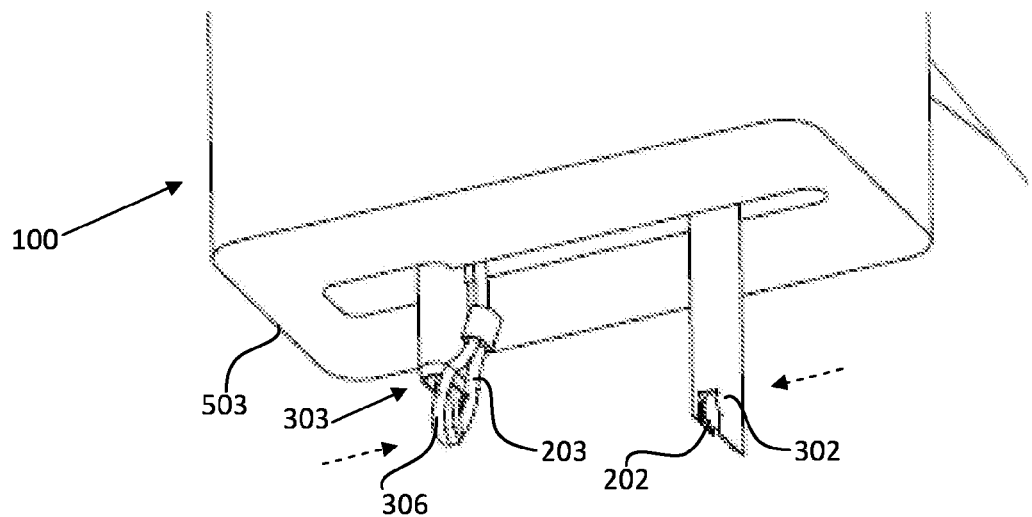
Figure 6D:
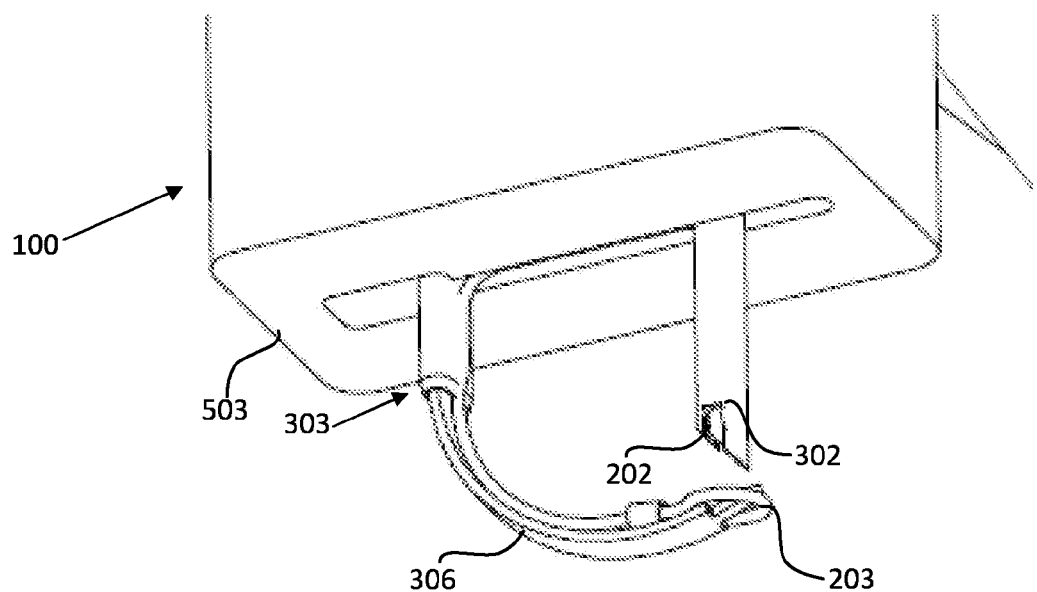
Figure 6E:
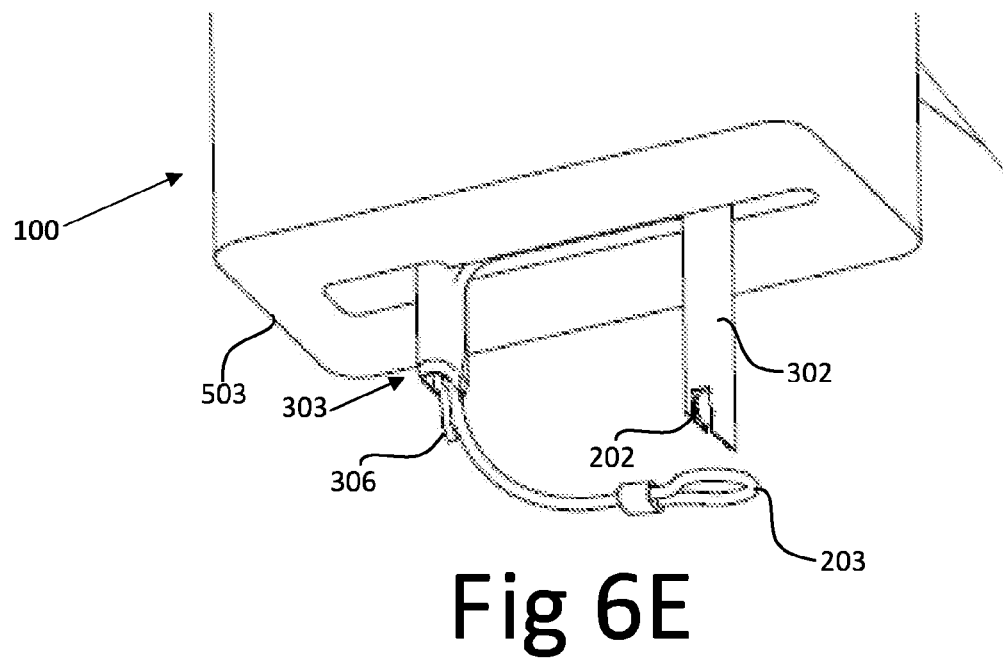
Figure 6F:
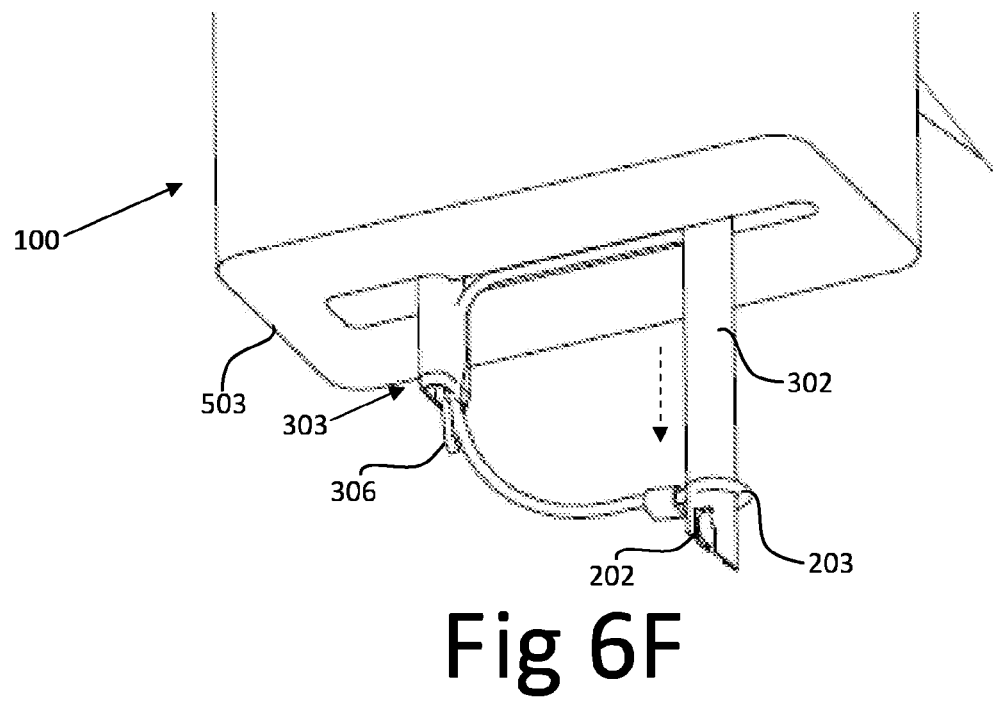
Figure 6G:
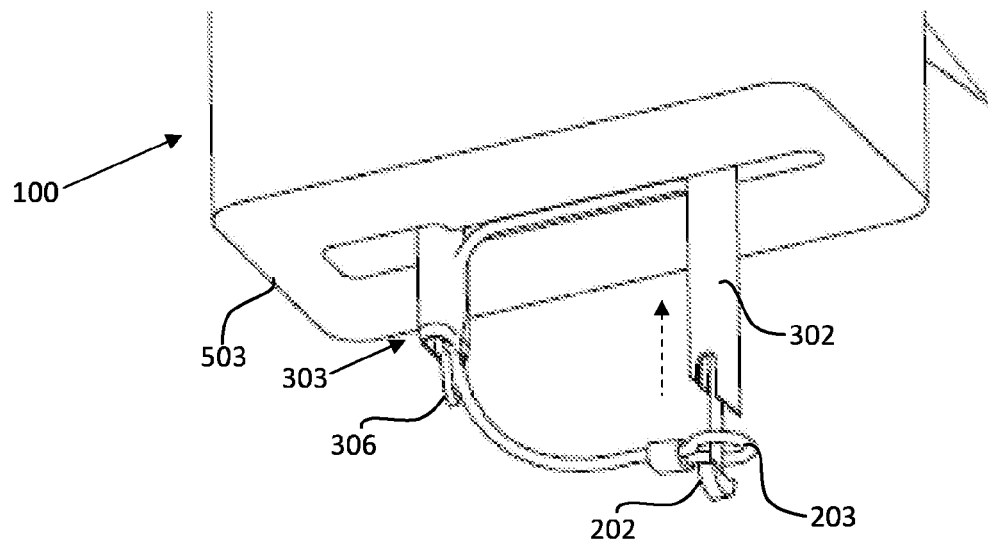
Figure 6H:
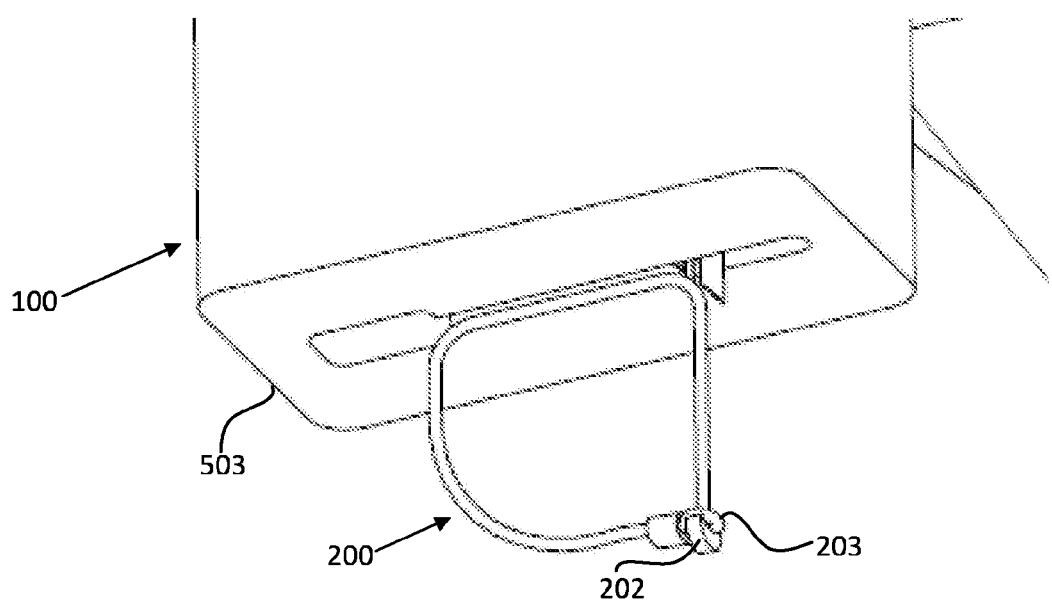

At the first stage (FIG. 6A), distal tip 503 of fastening device 100 is pressed against the tissue with wound 500 located roughly at the center of said distal tip 503. Next, hook insertion needle 302 and loop insertion needle 303 are inserted to the tissue together with clip 200 (FIG. 6B) Then, the two needles 302 and 303 are brought together, bringing the sides of the wound together (FIG. 6C). Then, as shown in FIGS. 6D-6H, the clip is applied and secured in a similar way as described above in reference to FIGS. 3C-3G, resulting in clip 200 passing thorough both sides of wound 500, thus closing the wound.

In certain embodiments, fastening device 100 can hold at least one and preferably two or more of clip 200. Once one clip is applied to the tissue, another clip 200 is loaded on hook insertion needle 302 and loop insertion needle 303 in preparation to the next clip application.

Fastening device 100 can be disposable or reusable. In the first case, fastening device 100 is delivered together with one or more of clip 200 and disposed of after use. If fastening device 100 is reusable, it is adapted for re-sterilization and clips can be provided separately in a cartridge than can be loaded before or during the operation. The cartridge can provide parts of the clip application mechanism (e.g. applicator section 101, insertion needles 302, 303).

A clip 200 can pass through the entire thickness of the tissue or can be embedded inside the tissue. Further, clip 200 can be applied manually, without the use of fastening device 100. To apply clip 200 manually, a suturing needle is attached to either of or both of the ends of clip 200 and used to insert clip 200 into tissue.

While described above in reference to FIGS. 2A and 2B as having a generally wire-like structure in which loop 203 can be made smaller by a cinching action through loop holder 204, a clip according to the invention can have other structures and forms.

FIGS. 7A-7C show a clip 250 according to certain embodiments. In certain embodiments, the clip is integrally formed. Clip 250 generally includes a body member 251 having a first member 253 at one end and a second member 252 at the other. As shown in FIGS. 7A-C, first member 253 includes a hook and second member 252 includes a loop.

Clip 250 further includes needle interface hook 261 at the loop end, and a hook-side needle interface hook 271 at the hook end. The loop end is characterized by aperture 265, that narrows towards the end of clip 250, i.e., the aperture has a wide section and a narrow section, the narrow section being distal to the wide section. Loop end further has insertion slope 277 and hook-side insertion slope 273, which can be, for example, beveled tips, to aid insertion of clip 250 through tissue.

Clip 250 generally includes at least one barb 269 at the hook end. When the hook end is inserted through aperture 265, as shown in FIG. 7B, one or more of barb 269 (two are shown) tend to prevent retraction of the hook end out of and away from the loop end. As shown in FIGS. 7A-7C, each of barbs 269 has a fin-like structure and is adapted to be bent during insertion. Further, in certain embodiments, aperture 265 of first member 253 is dimensioned to be not substantially larger than second member 252. For example, the width defined by one or more of barb 269 can be greater than the width defined by aperture 265 at its widest point. Insertion of second member 252 through aperture 265 generally involves either of second member 252 or first member 253 deforming slightly for insertion. The fin-like structure of barb 269 can bend towards body 251, first member 253 can stretch, first member 253 and second member 252 can twist relative to one another, or a combination thereof. Deformation can be elastic (return to original conformation) or plastic or a combination thereof.

As shown in FIG. 7B, tension on clip 250 will tend to slide second member 252 towards the narrow portion of aperture 265. This results in the locked conformation illustrated in FIG. 7C, in which the stem part of second member 252 (e.g., a portion substantially similar in cross section to that of body member 251) is slid into and occupies the narrowest part of aperture 265. This serves to lock clip 250 into a closed conformation.

As shown in FIG. 7A, second member 252 can include needle interface hook 271 while the loop-end includes loop interface hook 261. Needle interface hook 271 and loop interface hook 261 are illustrated as protrusions that generally taper to be smaller extending towards an end of clip 250. As shown in FIG. 7A, these interface hooks include a back portion that presents a push-able surface towards the main body portion of clip 250. In certain embodiments, one or both of these push-able surfaces are presented by indentations into clip 250 or other structures. The function of needle interface hook 271 and loop interface hook 261 are illustrated in FIGS. 8A and 8B.

Figure 8A:
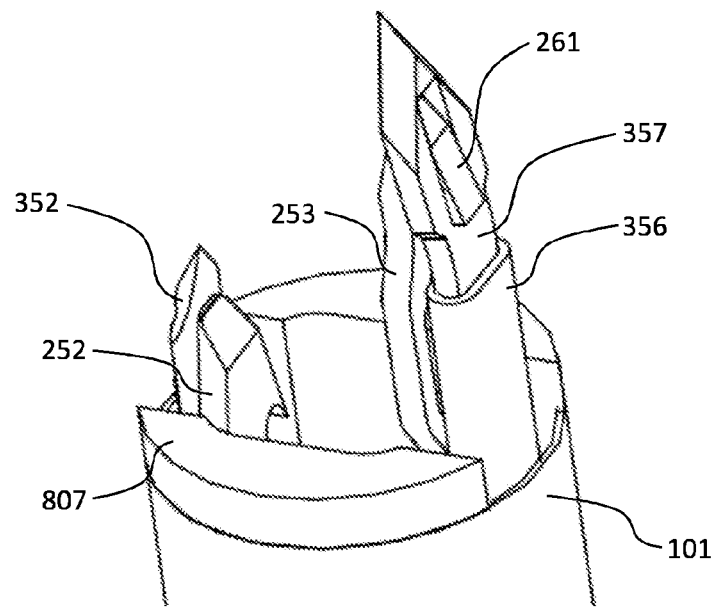
FIGS. 8A and 8B illustrate operation of a delivery tip of a fastening device.
Figure 8B:
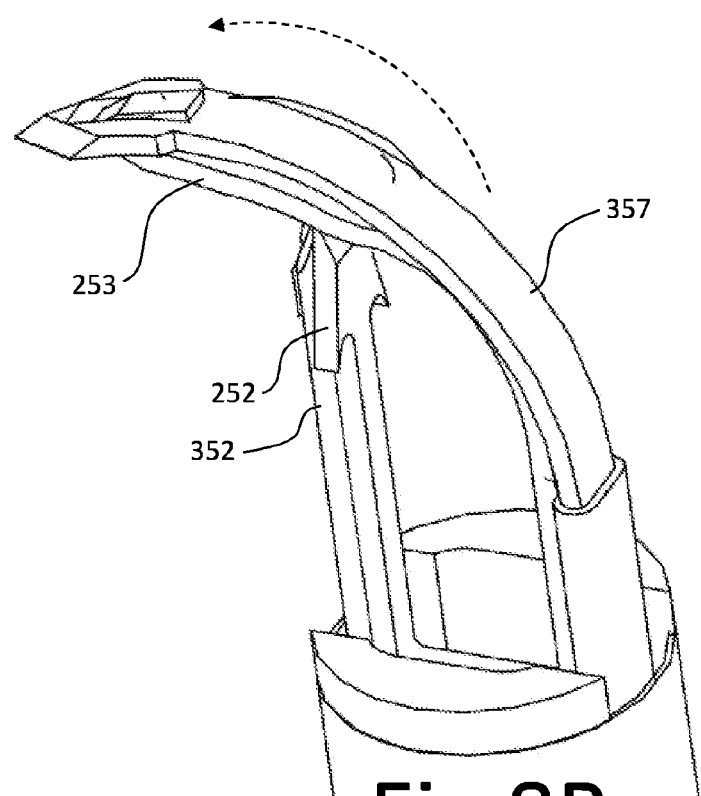

As shown in FIGS. 8A and 8B, the delivery tip of applicator section 101 of fastening device 100 provides a mechanism for delivering clip 250 to tissue and fastening it there. Hook insertion needle 352 is slidably disposed within applicator section 101 and configured to interface with second member 252 via needle interface hook 271. Loop insertion needle 357 extends from insertion tube 356 and similarly interacts with first member 253 via loop interface hook 261. As shown in FIG. 8A, applicator section 101 optionally includes a spacer 807 to assist in precise positioning of clip 250. Applicator section 101 and spacer 807 are part of a fastener carrier at least partially disposed within shaft 103 and carrying a plurality of clip 250.

FIG. 8B in combination with FIG. 8A illustrates the coordinated functioning of the insertion needles of applicator section 101. As shown in FIGS. 8A and 8B, hook insertion needle 352 has and maintains a substantially straight conformation as it assists in driving a hook end of clip 250 into tissue. Loop insertion needle 357 has a shape memory material such that, when the needle is contained within applicator section 101, the needle exhibits a shape substantially similar to, or governed by, a shape of applicator section 101. When loop insertion needle 357 is extended from applicator section 101, loop insertion needle exhibits a curved shape (FIG. 8B).

Applicator section 101 is configured to deliver clip 250 by pushing each of its ends into tissue. Delivery is coordinated by the independent translation of push rods (not shown in FIGS. 8A and 8B) operably coupled to hook insertion needle 252 and loop insertion needle 357. Coordination of delivery involves extending hook end of clip 250 away from applicator section 101 while also extending loop end of clip 250 and bringing the two ends of the clip together (e.g., through the operation of a shape memory material in loop insertion needle 357).

In certain embodiments, a leading edge of either or both of the insertion needles is at least partially sharpened to aid in penetration of tissue. Each of needle interface hook 271 and loop interface hook 261 can have a back surface that gets pushed by the corresponding insertion needle. Alternatively or additionally, either needle interface hook can include a slot and a portion of the corresponding insertion needle can be dimensioned to engage the slot. By these means, the needles can drive clip 250 into tissue and when the insertion needles are retracted, they disengage with clip 250 leaving it in place and fastened in a closed loop.

Figure 9A:
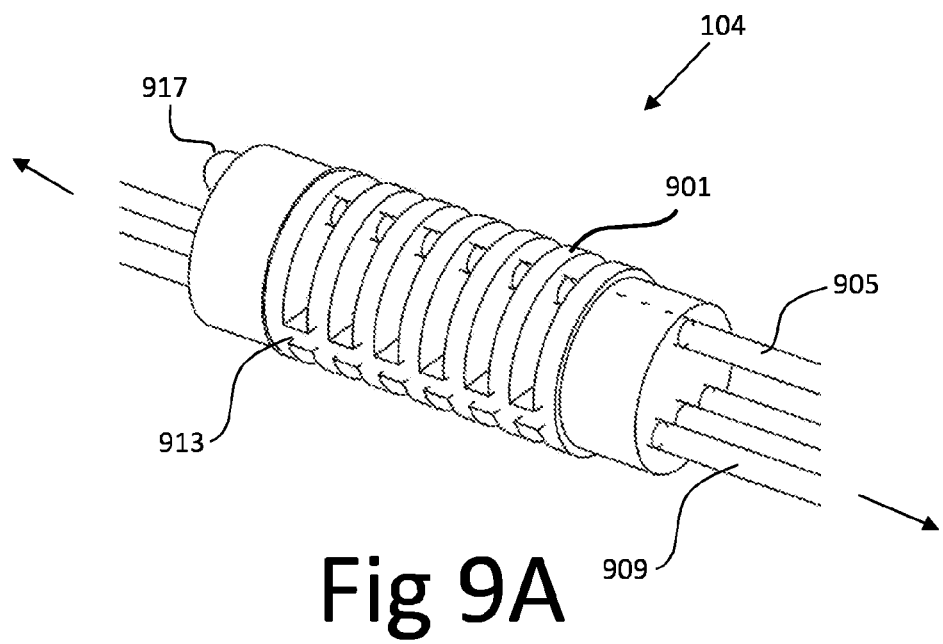
FIGS. 9A and 9B show an articulation joint.
Figure 9B:
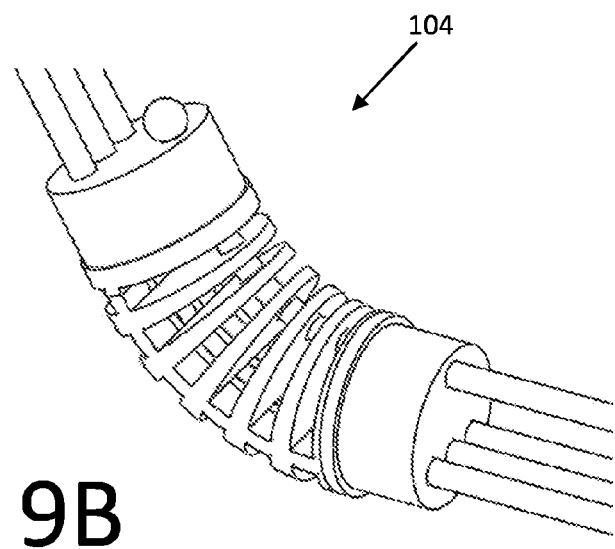

With reference to FIG. 1B, applicator section 101 and shaft 103 can include articulation joint 104. FIGS. 9A and 9B show a structure by which articulation joint 104 can allow shaft 103 to bend while still operating according to the embodiment described herein. As shown in FIG. 9A, articulation joint 104 includes a plurality of living hinge 913. A living hinge 903 generally includes a flexible portion and a flange 901. One or more of push rod 909 extend through joint 104 generally disposed so that, where there are multiple push rods, an axis of each push rod exhibits the same radius as the others when hinge 104 is bent. Flange 901 can be provided to limit the radius of curvature of hinge 104 to optimize functionality of applicator section 101, for example, by preventing the push rods from being bent too much.

Hinge 104 further includes an articulation cable 905 with an articulation wire ending 917 disposed on a distal side of hinge 104 from handle 102 (not pictured). When articulation wire 917 is pulled by a mechanism in handle 102 (discussed in more detail below), articulation wire ending 917 exhibits a compressive force on hinge 104, causing it to compress on one side, while expanding on the other, thus forming a bend in shaft 103, as shown in FIG. 9B.

Articulation joint 104 can be made with any suitable material known in the art such as, for example, an elastically deformable material. In certain embodiments, the material is a low friction material such as PTFE to minimize friction between joint 104 and push rod 909.

The fastening device is designed and dimensioned for use in laparoscopic or endoscopic surgery. Shaft 103 is dimensioned for use with endoscopic tubes and apparatuses. The device can also be inserted through an incision or trocar and used within a body. In certain embodiments, fastening device 100 can hold at least one of clip 250 in a cartridge 801 that can be interchangeably loaded into applicator section 101 of fastening device 100.

Figure 10:
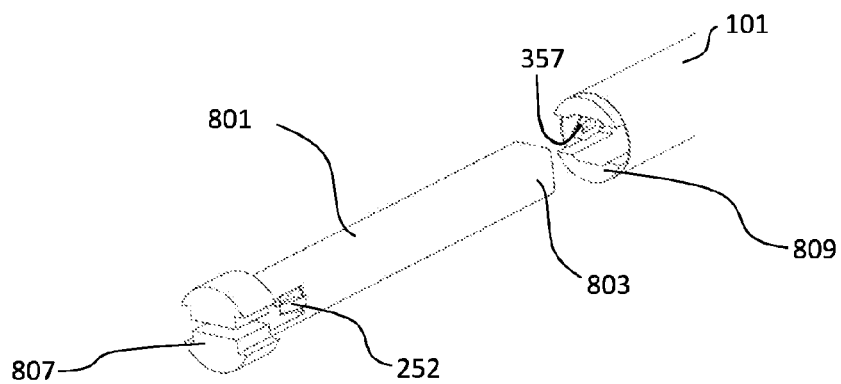
FIG. 10 shows a clip cartridge.

FIG. 10 shows a cartridge-style carrier 801 having an insertion end 803 and a spacer 807 oriented for insertion into applicator section 101. At the end of applicator section 101, FIG. 10 shows receiving pad 809 with loop insertion needle 357 visible disposed therein. As can be seen depicted in the distal end of cartridge 101, second member 252 (specifically, a portion of needle interface hook 271) is held in a slot, oriented to interface with hook insertion needle 352 in applicator section 101 (not visible in FIG. 10). Receiving pad 809 can include an interior shape dimensioned to receive insertion end 803.

Cartridge-style carrier 801 has a structure that cooperates with the mechanical structure of fastening device 100 so that the device can deliver and fasten clips within a body of a patient. Cartridge-style carrier 801 accommodates clips of different sizes.

In some embodiments, cartridge 801 uses an interchangeable spacer and spacers of different sizes accommodate different clips. In certain embodiments, each cartridge holds a number of clips of the same size. Spacers are provided to control the distance between the tip of the device and the tissue (or prosthesis) surface. For example, for smaller clips, a larger spacer is provided to prevent the clip from penetrating too deeply into the tissue. Similarly, for larger clips, a smaller spacer allows for good penetration depth of the clip.

Figure 11:
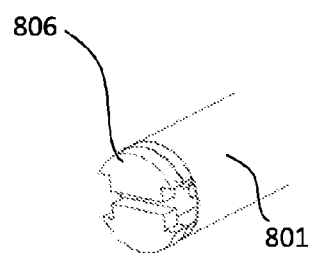
FIGS. 11-13 show clip cartridges for use with different sized clips.
Figure 12:
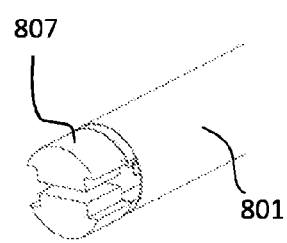
Figure 13:
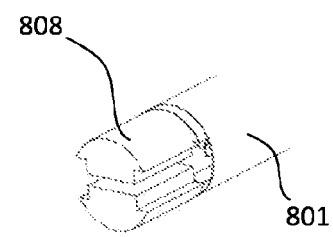

FIG. 11 shows a thin spacer 806 for use with larger clips. In some embodiments, the spacers are not interchangeable but instead formed as part of a disposable cartridge 801. FIG. 12 shows a spacer 807 for use with intermediate clips. FIG. 13 shows a long spacer 808 for use with small clips. As shown in FIGS. 10-13, a spacer may include a clip release slot disposed at an end of the body of the cartridge. In certain embodiments, cartridge 801 can be inserted into an end of an shaft 103 via insertion end. Spacers 806, 807, and 809 each provide a part of a fastener carrier operably connected to and at least partially disposed within shaft 103 and carrying a plurality of clip 250.

As can be seen in FIG. 10, when cartridge-style carrier 801 is inserted into shaft 103, second member 252 makes contact with hook insertion needle 352 via needle interface hook 271 and first member 253 makes contact with loop insertion needle 357. Clip 250 is delivered to tissue by the action of push rods that drive the insertion needles. Each push rod, and thus each needle, translates parallel to an axis of shaft 103 relative to each other as well as to member 103. In some embodiments, the clips are stacked one on top of the other inside cartridge 801; during each clip application cycle, a single clip is connected to the said insertion needles and then inserted into the tissue. At the end of the application cycle, a clip is advanced to the top of the cartridge in preparation to the next application cycle. In another embodiment cartridge-style carrier 801 includes an indicator which visually indicates to the surgeon the quantity of clips that remains in the cartridge. Motion of the push rods is governed by the mechanical structure of applicator 100.

Figure 14:
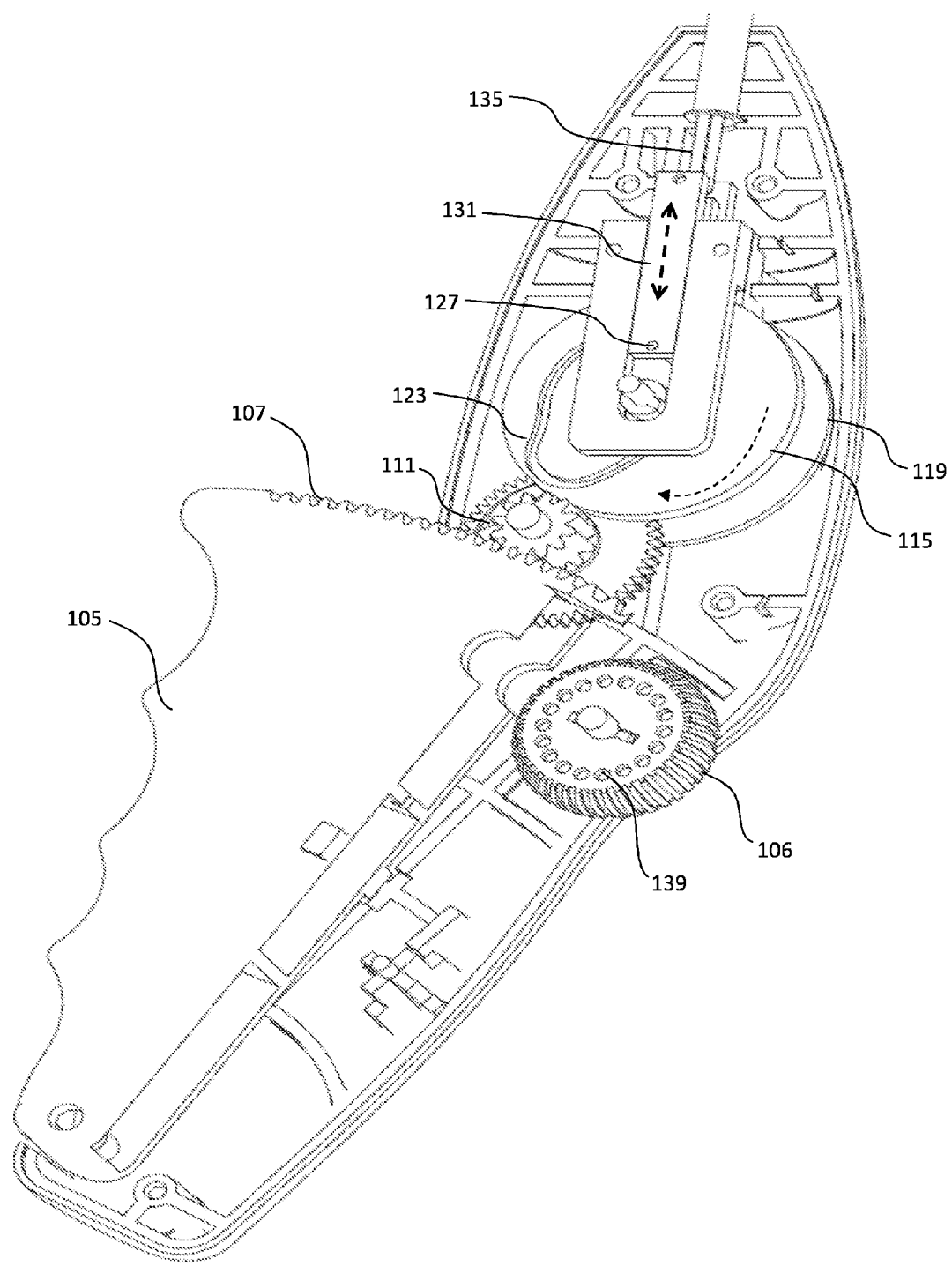
FIG. 14 gives a view of components of a handle of a fastening device.

FIG. 14 shows components of a handle of a fastening device. As can be seen in FIG. 14, one or more of push rod 135 are linked to one or more of translator bar 131. Translator bar 131 has a pin 127 fixed into a slot 123 of slot wheel 115. As shown in FIG. 14, applicator 100 includes a second slot wheel 119. Additional slot wheels may be included. The rotation of the slot wheel is driven through gear mechanism 111 by a geared face 107 of trigger 105.

By the relationship of these parts, when trigger 105 is squeezed, each of the slot wheels rotate. Because each slot (e.g., slot 123) is irregularly shaped (e.g., not a circle concentric with slot wheel 115), the corresponding translator bar translates independently relative to handle 102 and with acceleration defined by the disposition of the slot. The independent translation of translator bar 131 causes the independent translation of push rod 135 which (looking back at FIGS. 8A and 8B) cause the independent action of hook insertion needle 352 and loop insertion needle 357, as described above.

In certain embodiments, the series of coordinated motions of the insertion needles, and the delivery of a clip, is operated and coordinated electronically. For example, applicator device 100 can include servomotors operably connected to a governing circuit and/or chip. A motor can drive the slot wheels. Or, motors can drive each push rod as governed by a chip executing instructions provided, for example, by a tangible, non-transitory computer memory such as, for example, a field-programmable gate array or a disc drive.

Where shaft 103 includes articulation joint 104, articulation knob 106 controls the flexure of joint 104. Knob 106 is rotated by a user (e.g., with a thumb). During the rotation, articulation cable 905 (shown in FIGS. 9A and 9B) is wrapped around the knob's axis, pulling it toward the handle, articulating joint 104. Knob 106 can include one or more of socket 139 adapted to fit a ball plunger in place once a desired degree of articulation is obtained.

The invention further provides methods for closing a wound that involve deploying fastening device 100 to deliver a clip to a wound. Wound closure according to methods of the invention involves positioning the delivery tip close to the wound. Where the wound is inside the body, the shaft 103 is inserted through an incision, trocar, or endoscopic channel. A clip is delivered and formed into a closed configuration by device 100.

When a practitioner depresses trigger 105, loop insertion needle 357 extends from insertion tube 356 and interacts with first member 253 via loop interface hook 261. Hook insertion needle 352 has and maintains a substantially straight conformation as it assists in driving a hook end of clip 250 into tissue. When loop insertion needle 357 is extended out from applicator section 101, it curves to guide the fastening of the clip.

Clip 250 is delivered by pushing each of its ends into tissue. Delivery is coordinated by the independent translation of push rods operably coupled to hook insertion needle 252 and loop insertion needle 357, which is triggered through the use of trigger 105. Coordination of delivery involves extending hook end of clip 250 away from applicator section 101 while also extending loop end of clip 250 and bringing the two ends of the clip together (e.g., through the operation of a shape memory material in loop insertion needle 357). Methods include using the needles to drive clip 250 into tissue and retracting the needles so they disengage from clip 250 leaving it in place and fastened in a closed loop, closing the wound.

The invention also provides methods for securing a medical prosthesis to tissue. Securing the prosthesis is accomplished through delivering a clip to a target tissue that has a prosthesis applied to it, using applicator 100. Methods include inserting a distal portion of fastening device 100 into a patient's abdominal cavity through a trocar or through an incision. The distal end is pressed against the hernia mesh and a clip is delivered through the tissue and hernia mesh and secured in place by pressing trigger 105 on handle 102. Shaft 103 is then removed.

Delivery according to the methods of the invention causes the first end of the body to mate with and be retained by the second end of the body, thereby forming the clip into a closed configuration and securing the prosthesis to the tissue. The prosthesis can be secured by employing a fastening structure provided by the first and second members.

During delivery, hook insertion needle 352 interfaces with second member 252 via needle interface hook 271. Loop insertion needle 357 extends from insertion tube 356 and similarly interacts with first member 253 via loop interface hook 261.

Loop insertion needle 357 is extended out from applicator section 101 and curves to guide the clip through the prosthesis. Delivery is coordinated by the independent translation of push rods (discussed above) operably coupled to hook insertion needle 252 and loop insertion needle 357. Coordination of delivery involves extending hook end of clip 250 away from applicator section 101 while also extending loop end of clip 250 and bringing the two ends of the clip together (e.g., through the operation of a shape memory material in loop insertion needle 357). Methods can include pushing a clip through a back surface of needle interface hook 271 and loop interface hook 261 with a corresponding insertion needle. The needles can drive clip 250 into the prosthesis (e.g., hernia mesh). The needles are then retracted, leaving clip 250 in place and fastened in a closed loop securing the prosthesis to the tissue.

One insight of the invention is that in hernia mesh 400 fixation, it is important that a fastener, such as a tack or clip, should be anchored to a fascia layer. Fascia is a layer of fibrous tissue containing closely packed bundles of collagen. Fascia provides a connective tissue that surrounds muscles, groups of muscles, blood vessels, and nerves. This is the layer to which surgeons affix a hernia mesh and the fastener design should form a strong anchor to that layer.

In each patient the thickness of the pre-peritoneal fat layer is different. For example, the first fascia layer in obese patients is significantly deeper than in slim patients. Some existing fixed-length hernia tacks favor shorter lengths so that, in slim patients, they will not penetrate all the way through the abdominal wall and to the skin. Fasteners that are too small, however, will not anchor into the fascia in some sites or in obese patients for whom the pre-peritoneal fat layer is substantially thick. One insight of the invention is that there is a need for variable depth fasteners that can be delivered by a single device to accommodate variations in the abdominal wall of different patients and variation in areas of the abdominal wall at any treatment site. A fastening device of the invention is provided that can fix a hernia mesh despite variations in tissue with fasteners that pass beyond the hernia mesh by a controlled amount (e.g., between about 3 millimeters and 15 millimeters). By provided fasteners that extended only about a couple of millimeters past the hernia mesh, a fastening device of the invention provides good fixation to prevent recurrence of the hernia. By avoiding use of a fastener that is too long, post-operative pain is minimized. Considerations in fastener operation are discussed in Abhishek, et al., 2012, Laparoscopic Umbilical Hernia Repair: Technique Paper, ISRN Minimally Invasive Surgery, pp. 1-4, Article ID 906405, and in Nguyen, et al., 2008, Postoperative Pain After Laparoscopic Ventral Hernia Repair: a Prospective Comparison of Clips Versus Tacks, JSLS 12:113-116, the contents of each of which are incorporated by reference.

Figure 15:
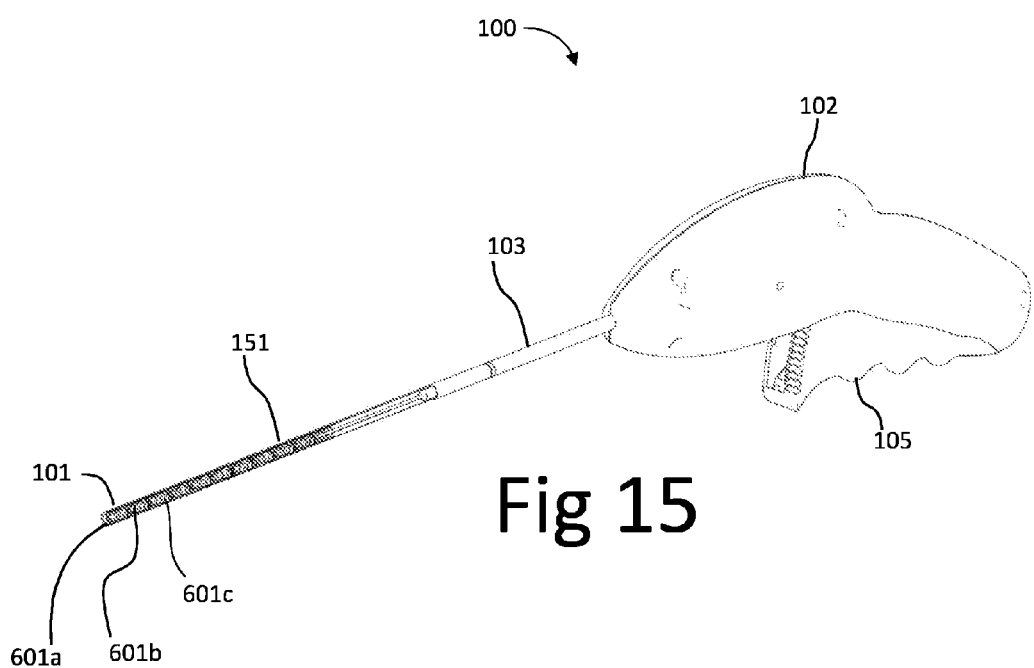
FIG. 15 depicts a fastening device for delivering fasteners of different sizes.

FIG. 15 depicts a fastening device 100 for delivering fasteners of different sizes. Device 100 generally includes a handle 102 connected through shaft 103 to applicator section 101. Handle 102 will generally include a trigger 105. Squeezing trigger 105 delivers one fastener into tissue. Device 100 includes a carrier 151 for a holding plurality of fastener 601. The fastener carrier 151 is operably connected to the shaft 103 by any suitable attachment mechanism. For example, a portion of shaft 103 can extend into carrier 151 or a portion of carrier 151 can extend into shaft 103. Additionally, the fitting between shaft 103 and carrier 151 can be threaded, press-fit, use adhesives, or a combination thereof. Shaft 103 and carrier 151 can be co-molded or manufactured as a single piece. The connection between shaft 103 and carrier 151 is operable in that operation of trigger 105 delivers a fastener from carrier 151. Fastening device 100 can provide variable depth fastening by allowing for the switching of cartridge 151 wherein each cartridge 151 contains a different length of fastener 601. Another way that device 100 can provided variable depth fastening is by allowing for the loading of different sizes of fastener 601 to a single device. Preferably, switching from one depth to another does not require any adjustment at the operation handle. For example, the first 4 of fastener 601 may be long with the rest being short (or a mixture of multiple sizes). In some embodiments, device 100 uses a stretchable fastener 601 and the fastener 601 penetration depth is adjusted through the stretching of fastener 601.

In FIG. 15, each fastener 601 is depicted as a helical hernia mesh fixation tack, although other embodiments discussed herein are within the scope of the invention. In some embodiments, cartridge 151 is a replaceable cartridge. A replaceable cartridge can be provided that is pre-loaded with a selection of fastener 601. Helical fasteners that may be adapted for use with device 100 are discussed in U.S. Pat. No. 8,282,670; U.S. Pat. No. 8,216,272; and U.S. Pat. No. 8,114,099, the contents of which are incorporated by reference. In some embodiments, a fastener may have tapered portions of a shaft, such as those shown in U.S. Pub. 2004/0098045.

FIGS. 15-19 depict embodiments based on a helical fastener 601 and cartridge 151. The depth may be adjusted by replacing a cartridge 151 during or prior to the operation or by loading cartridge 151 with a mixture of fastener 601. In some embodiments, the fasteners 601 are arranged around a central pivot which rotates the fasteners. The internal surface of the tube is threaded such that as each fastener 601 is rotated it is advanced forward and the first one is threaded into the mesh 400 and the tissue. Handle 102 generate the same number of rotations per each stroke of the activation lever.

Figure 16:
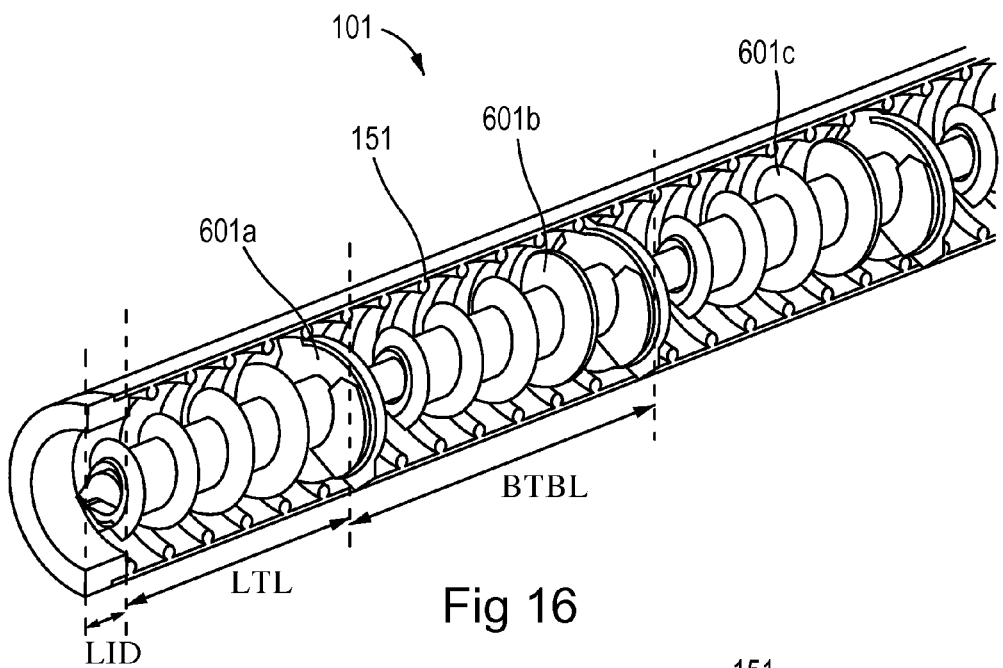
FIG. 16 shows a carrier loaded with long tack-style fasteners.

FIG. 16 shows applicator section 101 with cartridge 151 loaded with tack-style fasteners 601 of size that provides a long tack length (LTL). Cartridge 151 can be provided as a replaceable cartridge portion of applicator section 101. Preferably, cartridge 151 includes a plurality of fastener 601 arranged such that each fastener 601 will be completely delivered into the tissue for each complete stroke of the operational trigger. When the central pivot is rotated, the foremost fastener 601 will advance a certain amount, and "idle depth", before it engages tissue. This long-fastener idle depth (LID) is defined in-part by the distance between the base of one fastener and the tip of the adjacent fastener. Generally, the LTL corresponds to the threaded shaft of a fastener and the LID corresponds to the spacing between fasteners. Together, these contribute to the base-to-base length (BTBL), indicating the length of cartridge 151 that is dedicated to each fastener 601.

Figure 17:
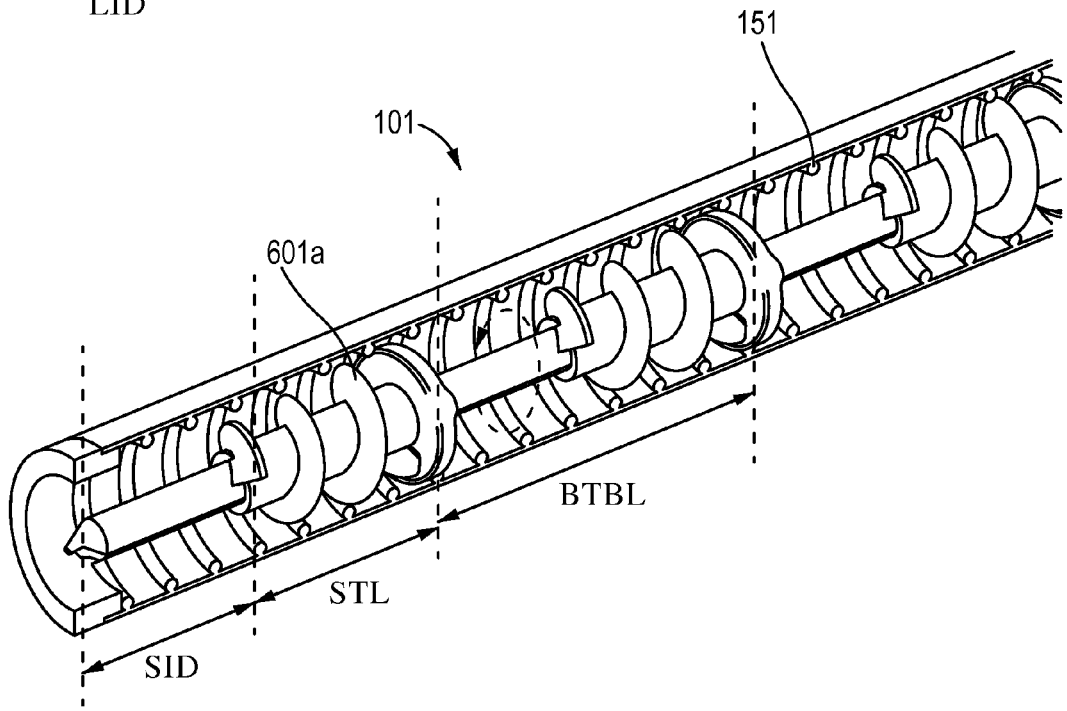
FIG. 17 shows an insert loaded with short tack-style fasteners.

FIG. 17 shows applicator section 101 with cartridge 151 loaded with tack-style fasteners 601 of a size that provides a short tack length (STL). FIGS. 16 and 17 show that for every type of cartridge 151, fasteners 601 may be arranged at the same distance, or base-to-base length (BTBL) from one another. Each fastener 601 is rotated inside the device for an idle distance such that it will not be over rotated inside the tissue. For a fastener 601 of a short tack length (STL), the short-fastener idle distance short (SID) is longer than the long-fastener idle distance long (LID) in the case of the longer fastener 601. Turning now to FIGS. 18A-19B, the use of fastening device 100 to deliver fasteners 601 through hernia mesh 400 and peritoneum 405 to the abdominal wall 401 is illustrated.

Figure 18A:
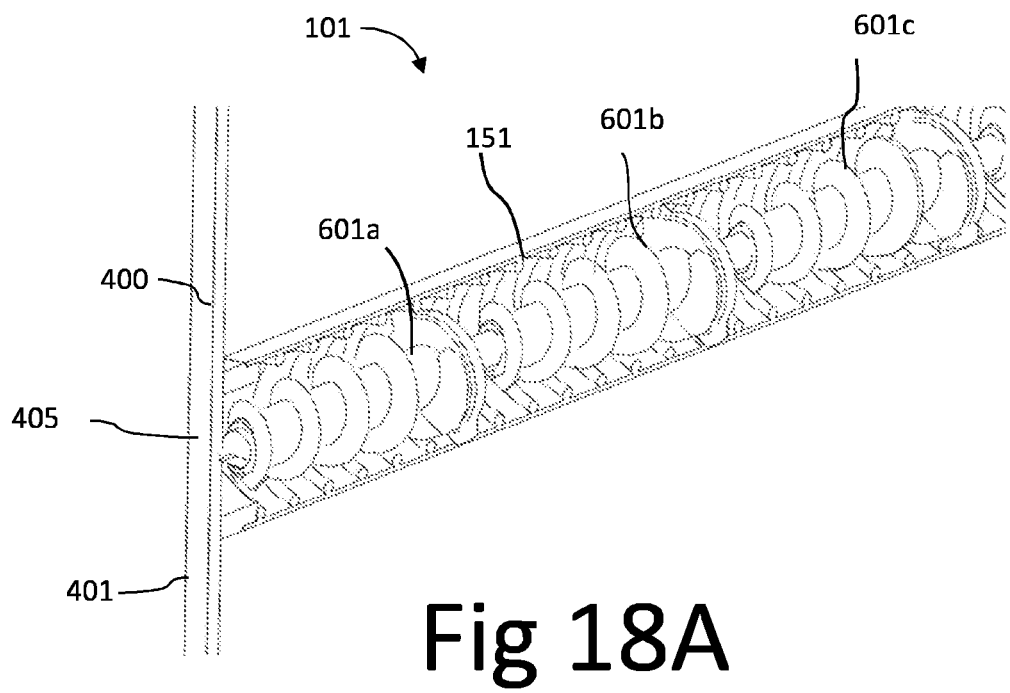
FIGS. 18A and 18B show a carrier loaded with long helical fasteners.
Figure 18B:
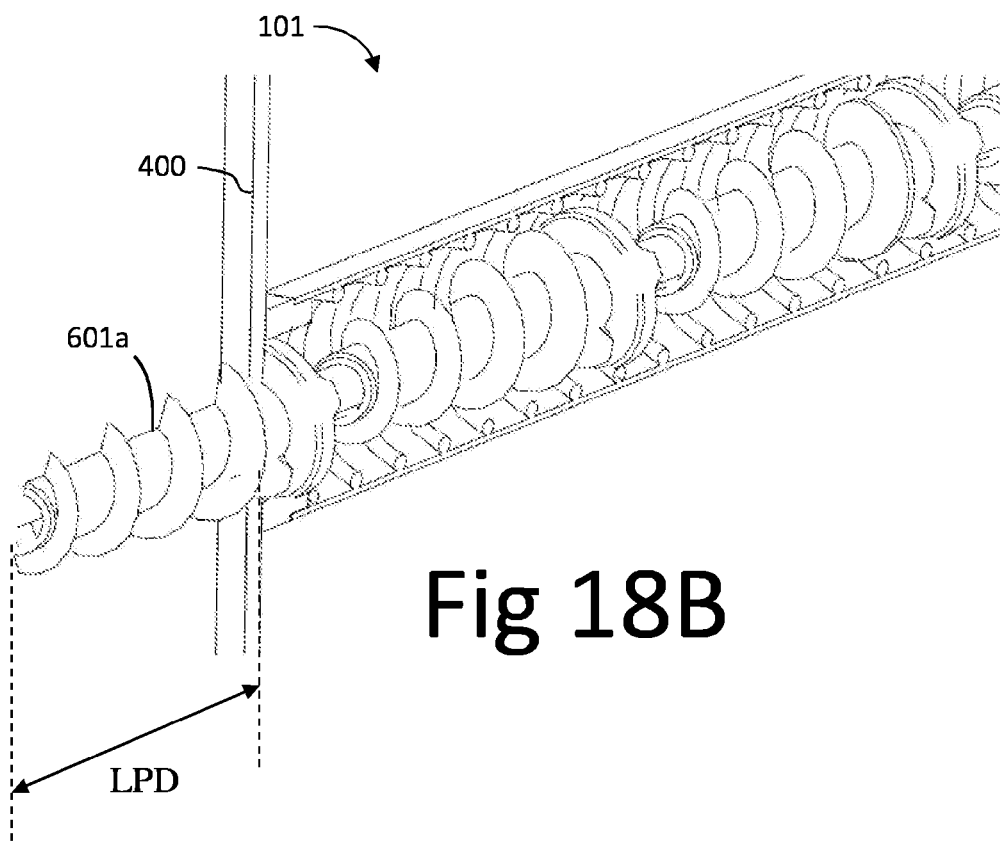

FIGS. 18A and 18B show a cartridge 151 with a plurality of helical fastener 601 each having a long length. Operation of trigger 105 drives a fastener 601 through hernia mesh 400 and peritoneum 405 to the abdominal wall 401. As shown in FIG. 18A, insert 151 includes a plurality of fasteners 601a, 601b, 601c, etc. Here, fastener 601a, for example, offers a long penetration depth (LPD) as shown in FIG. 18B.

Figure 19A:
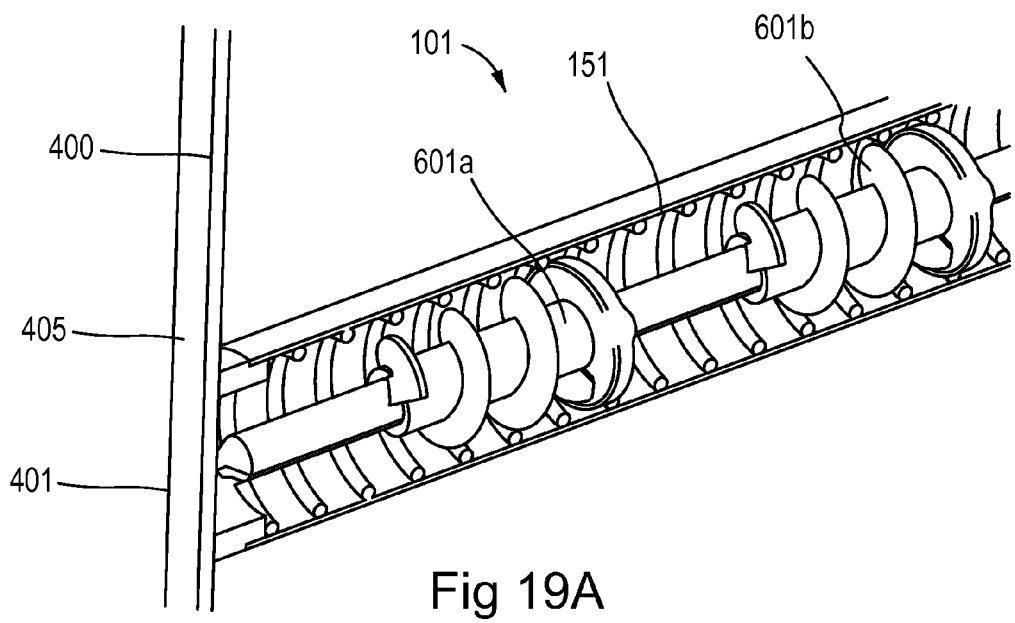
FIGS. 19A and 19B show a carrier loaded with short helical fasteners.
Figure 19B:
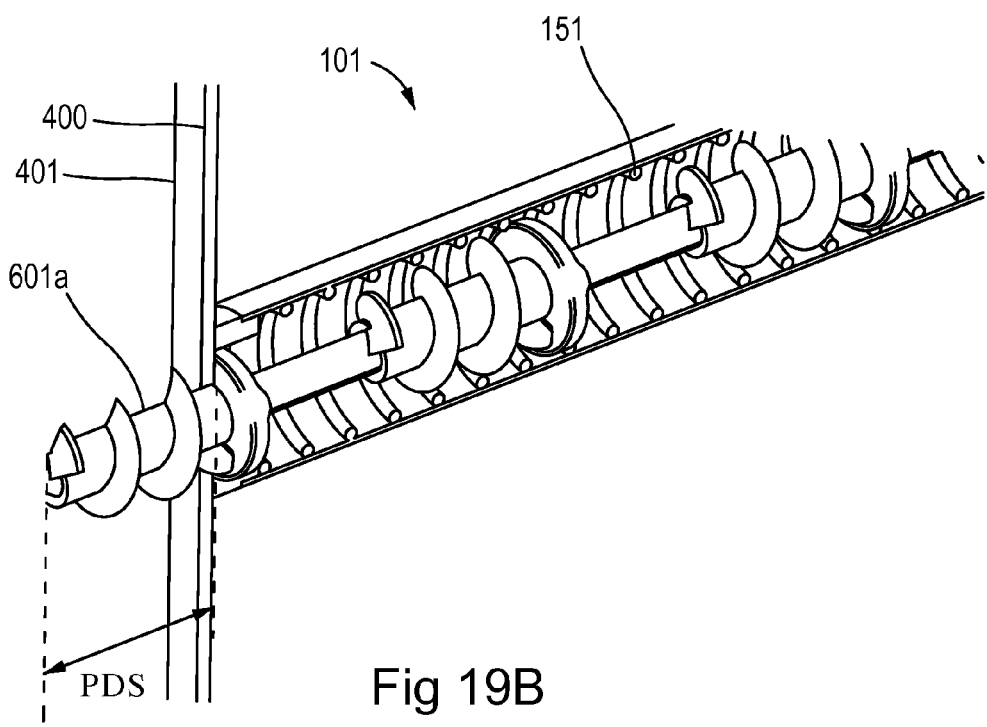

FIGS. 19A and 19B show cartridge 151 with a plurality of helical fastener 601 each having a short length. Here, fasteners 601a, 601b, 601c, etc. each offer a short penetration depth (PDS).

In certain embodiments, the invention provides a fastening device 100 in which a cartridge 151 is configured to accept anchor-style fasteners 611 of different sizes. Anchor-style fastener 611 will generally include at least one barbed strut. In some embodiments, each anchor-style fastener 611 includes two barbed struts in a generally U-shaped configuration (e.g., V-shaped, J-shaped, or others may be provided). Barbed fixation devices are discussed in U.S. Pat. No. 7,959,640; U.S. Pat. No. 6,447,524; U.S. Pub. 2012/0016389; and U.S. Pub. 2004/0204723, the contents of which are incorporated by reference. In some embodiments, a mesh fastener may have hybrid characteristics such as, for example, a helical barb, such as those described in U.S. Pat. No. 8,034,076.

Figure 20A:
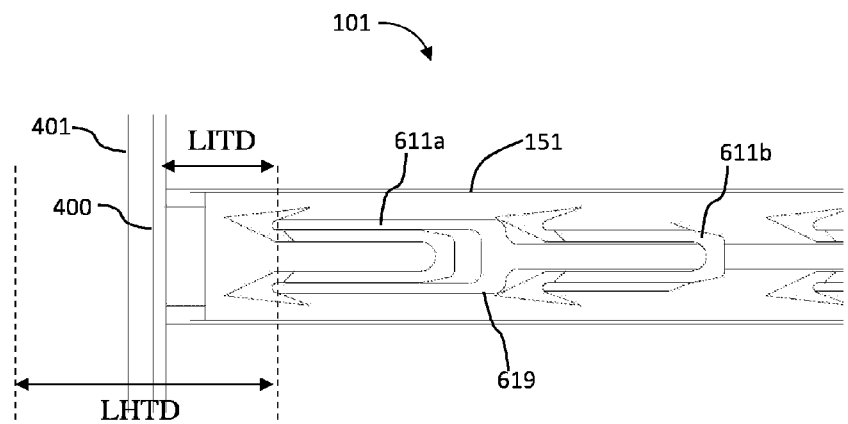
FIGS. 20A and 20B show a carrier loaded with long anchor-style fasteners.
Figure 20B:
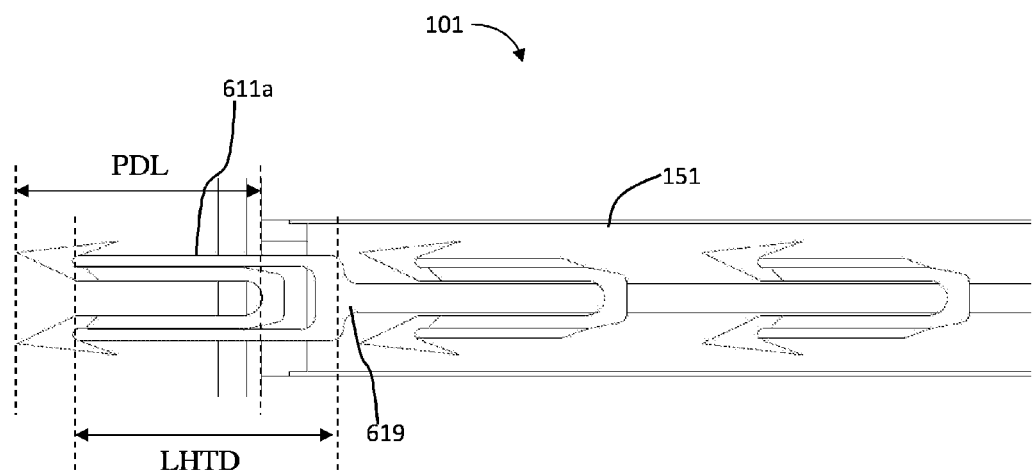

FIGS. 20A-21B show an applicator section 101 of fastening device 100 having a cartridge 151 for delivering a plurality of fastener 601 having an anchor style. FIGS. 20A and 20B show cartridge 151 with anchor-style fastener 611 of a long size disposed therein. Each operation of trigger 105 causes hammer 619 to travel a long-fastener hammer travel distance (LHTD). When delivering an anchor-style fastener 611 of a long size, hammer 619 will travel a long-fastener internal travel distance (LITD).

The anchor-style fasteners 601 are inserted into the tissue by pushing them forward using a reciprocal moving hammer 619. Hammer 619 scoops only the first fastener 601. An additional mechanism such as a spring positions each new fastener 601 in front of the hammer 619. For any version of a cartridge 151, hammer 619 moves the same distance back and forth. In a similar way to the helical fastener 601 cartridge 151, the difference between the versions is the length in which the fastener 601 is moving inside and outside the device.

Figure 21A:
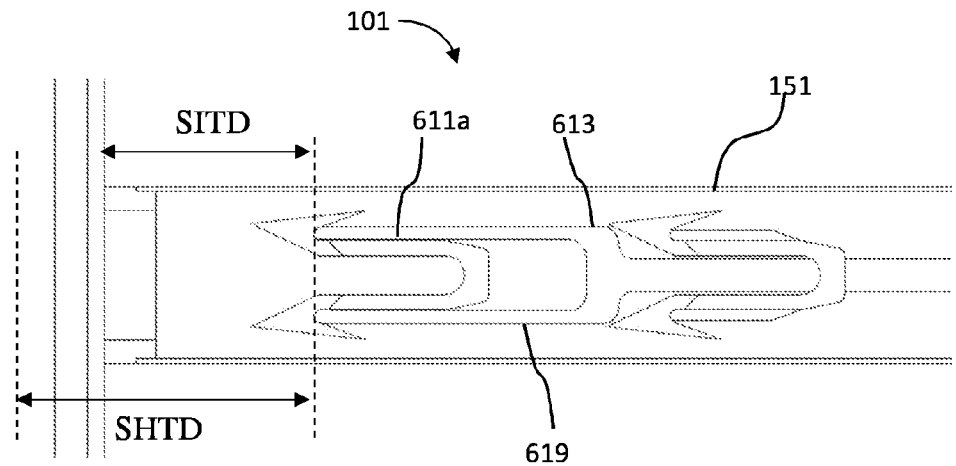
FIGS. 21A and 21B show a carrier loaded with short anchor-style fasteners.
Figure 21B:
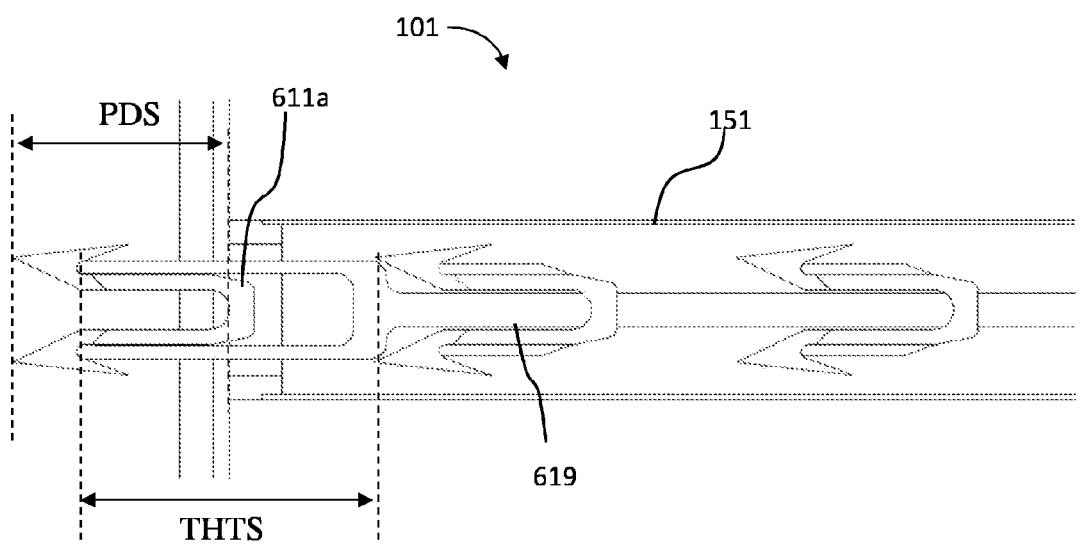

FIGS. 21A and 21B show the short version of cartridge 151 for anchor-style fastener 611. FIG. 21A shows applicator section 101 carrying cartridge 151 for anchor-style fasteners 601 of a short size. Each operation of trigger 105 causes hammer 619 to travel a short-fastener hammer travel distance (SHTD). When delivering an anchor-style fastener 611 of a short size, hammer 619 will travel a short-fastener internal travel distance (SITD) In the case of the shorter anchor-style fastener 611, hammer 619 will travel a longer distance inside the device (i.e., SITD>LITD). However, hammer 619 moves the same distance for each anchor-style fastener 611 (i.e., LHTD=SHTD). In certain embodiments, the invention provides a fastening device 100 for delivering clip-style fasteners 250 of different sizes. Device 100 generally includes a handle 102 connected through shaft 103 to applicator section 101. Handle 102 will generally include a trigger 105. Device 100 includes a cartridge-style insert 801, substantially as shown in FIGS. 8A, 8B, and 10-13, for a holding plurality of clip-style fastener 250.

FIGS. 22A-23B show a cartridge-style insert 801 for delivering a plurality of a clip-style fastener 250. The concept for the clip-style fastener 250 having a plurality of lengths is similar to the anchor-style fastener 611. There are two insertion needles which insert and engage the two ends of the clip like fastener 601. Handle 102 is configured to deploy these needles as discussed above with respect to FIGS. 1-14. For clip-style fastener 250 of a short length, needles 352 and 357 travel a larger distance inside shaft 103 to compensate for the shorter length of the clip-style fastener 250.

Figure 22A:
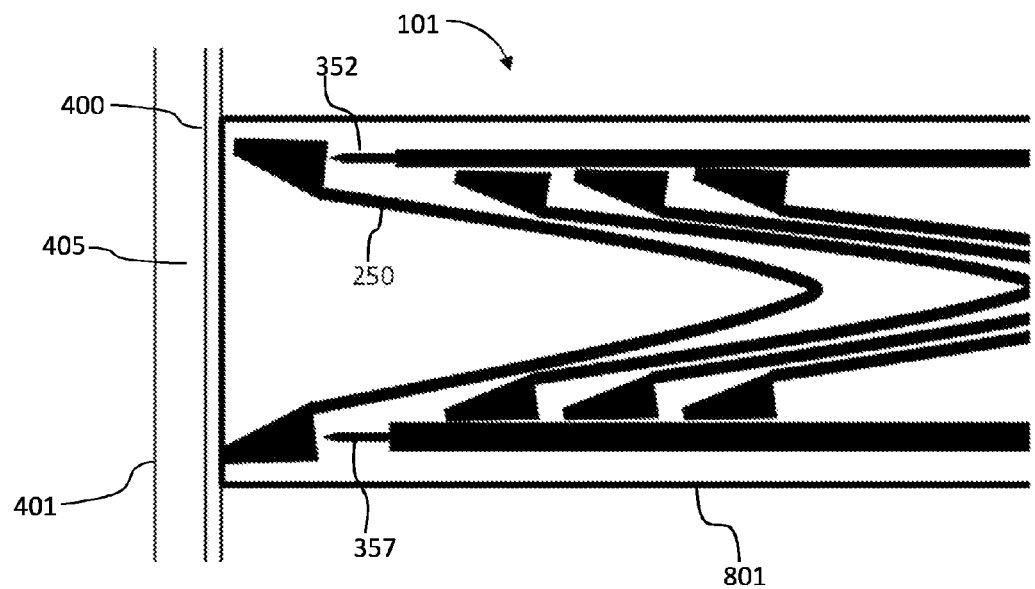
FIGS. 22A and 22B show a carrier loaded with long clip-style fasteners.
Figure 22B:
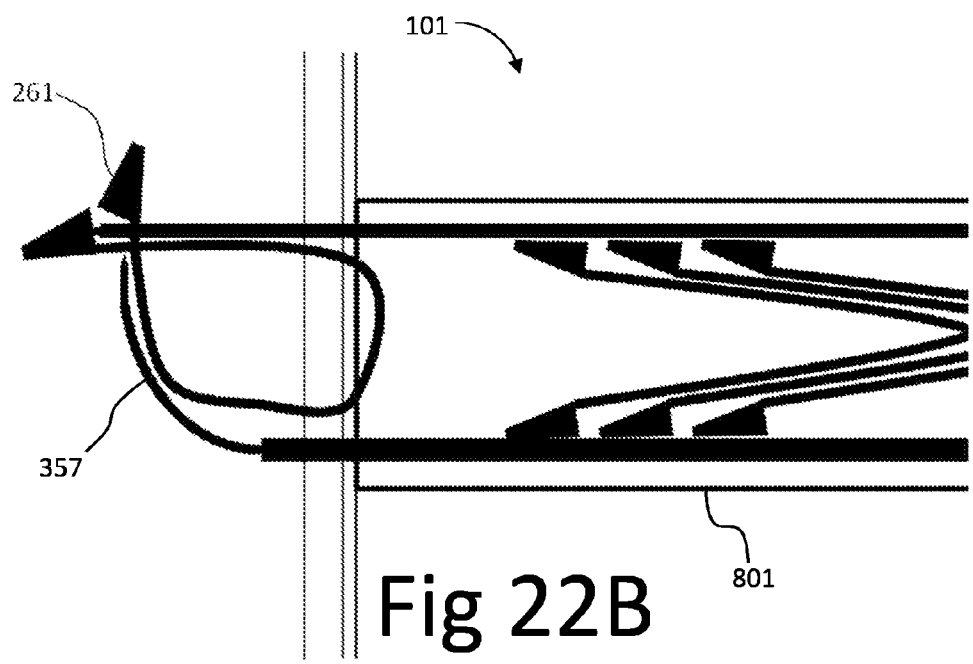

FIGS. 22A and 22B show a fastening device 100 delivering a plurality of clip-style fastener 250 having a long size.

Figure 23A:
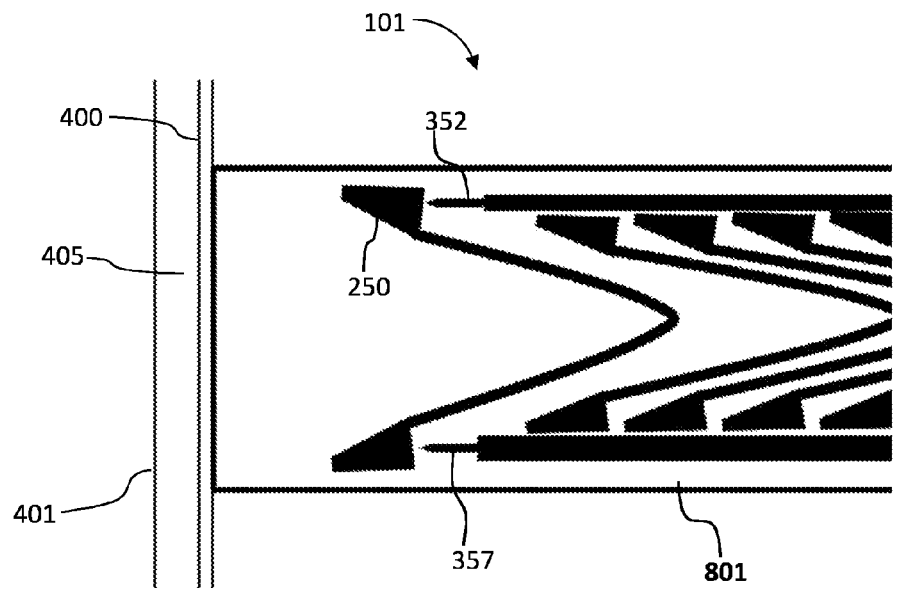
FIGS. 23A and 23B show a carrier loaded with short clip-style fasteners.
Figure 23B:
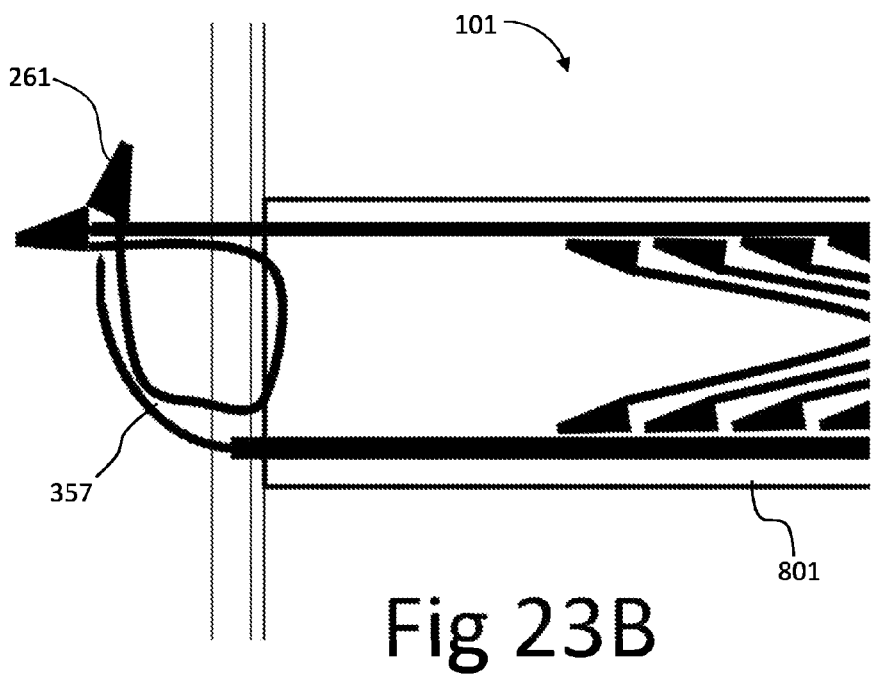

FIGS. 23A and 23B show a fastening device 100 delivering a plurality of clip-style fastener 250 having a short size. The operation of device 100 for delivering clip-style fastener 250 is discussed in detail above. FIGS. 10-13 depict use of a spacer to accommodate different sized clips (e.g., fasteners or clips) and FIGS. 31-35 show detail of a delivery mechanism.

Figure 24:
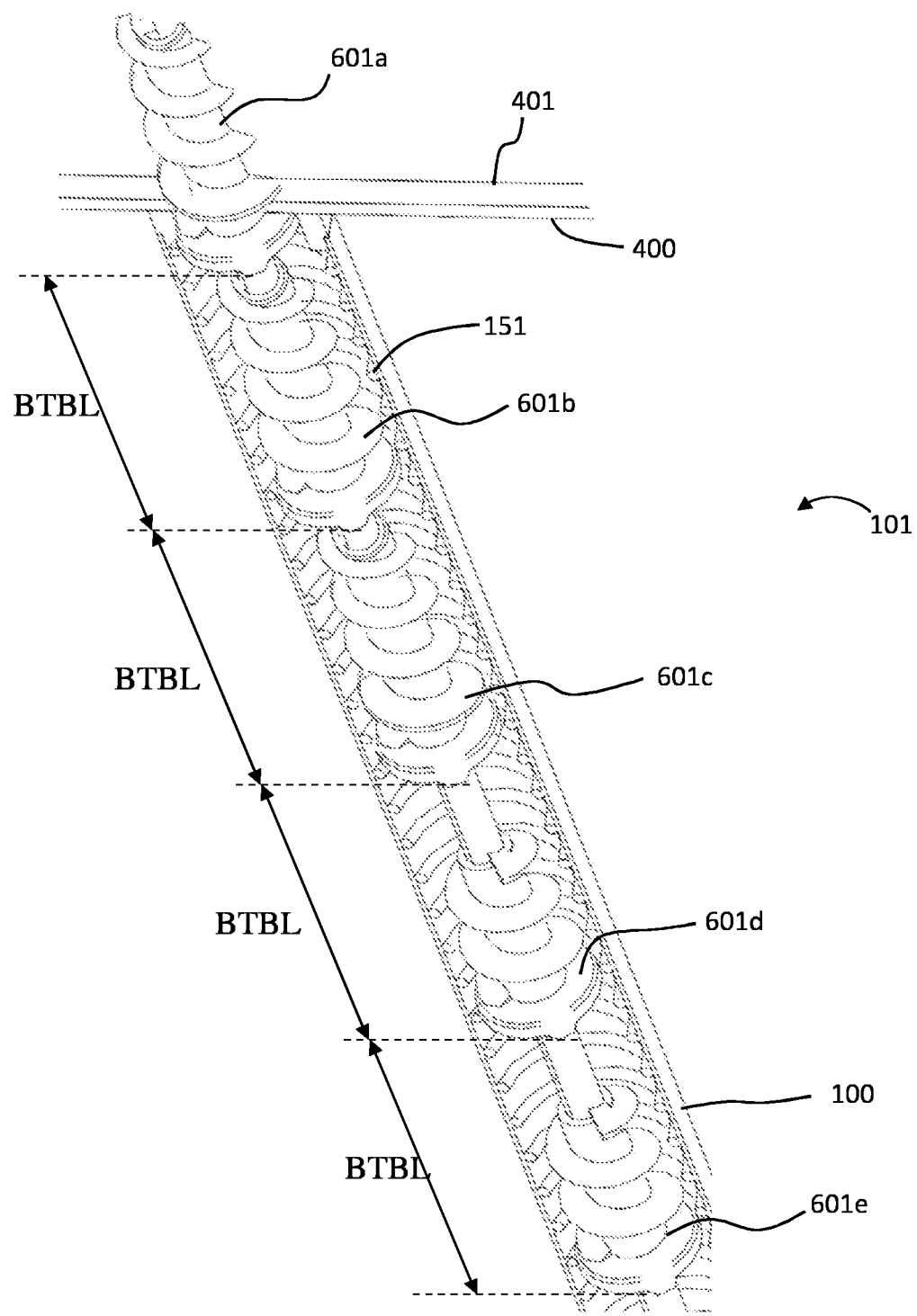
FIG. 24 shows a carrier loaded with tack-style fasteners of a plurality of sizes.

FIG. 24 shows applicator section 101 with cartridge 151 loaded with tack-style fasteners 601 of a plurality of sizes. Here, tack-style fasteners 601a-601c are each of a long size and tack-style fasteners 601d and 601e are each of a short size. As shown in FIG. 24, at least two types of fastener 601 are arranged inside the device, e.g. the first three of fastener 601 are long of fastener 601 and rest are shorter. This allow the surgeon to apply different sized of fastener 601 without replacing a cartridge 151. If the surgeon doesn't want to apply any of a long fastener 601, each of the long fastener 601 can be ejected outside of the patient body before fastener 601 application. As before, the plurality of fastener 601 are arranged such that no adjustment at handle 102 mechanism is required. The base-to-base length (BTBL) between the base of each fastener is constant along a length of cartridge 151 regardless of a size of tack-style fasteners 601.

Figure 25:
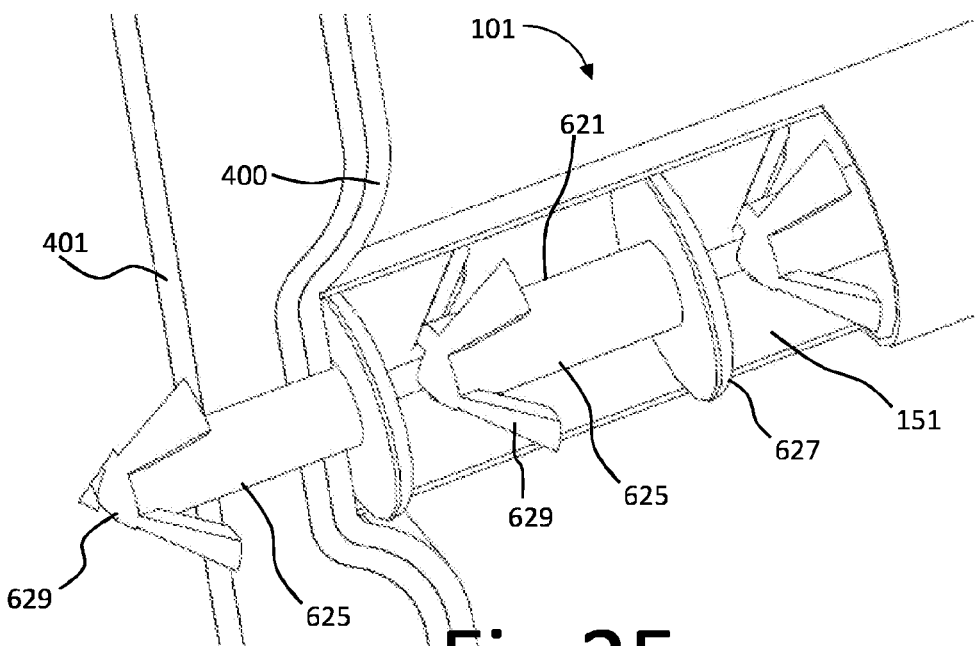
FIG. 25 shows shallow penetration of a stretchable fastener.
Figure 26:
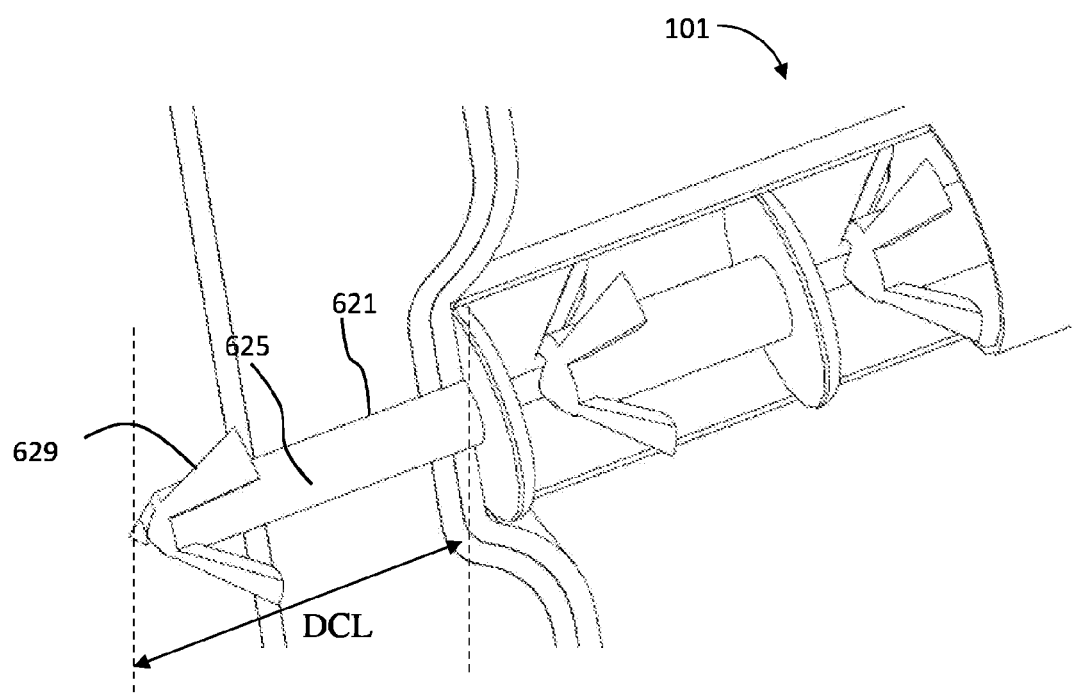
FIG. 26 shows deep penetration of a stretchable fastener 621.

FIGS. 25 and 26 illustrate a device 100 for delivering a plurality of stretchable fastener 621. Stretchable fastener 621 generally includes an elastic material such as, for example, a poly-urethane, silicon, polyester, polyamide (e.g., nylon), polyolefin (e.g., polyethylene or polypropylene), poly-urethane carbonate, polydioxane, animal gut such as chromated catgut, metal such as steel, tantalum, or a shape memory metal. Fastener 621 may include jacketed filaments such as twisted polyamide. This allows a surgeon to set the penetration depth of each individual stretchable fastener 621 at handle 102 without removing applicator section 101 from a patient. Once deeper penetration is set, the fastener tip 629 penetrates more into the tissue. Since the stretchable fastener 621 can be stretched, the final result is deeper penetration and longer stretchable fastener 621. As shown in FIG. 26, once the device is configured to penetrate deeper and a stretchable fastener 621 is delivered to tissue, the central core 625 of the stretchable fastener 621 is stretched to a deployed core length (DCL).

FIG. 25 shows shallow penetration of stretchable fastener 621. The deployed core length (DCL) (e.g., the distance between base 627 and fastener tip 629) is shorter than the deployed core length DCL depicted in FIG. 26

FIG. 26 shows deep penetration of a stretchable fastener 621.

Figure 27A:
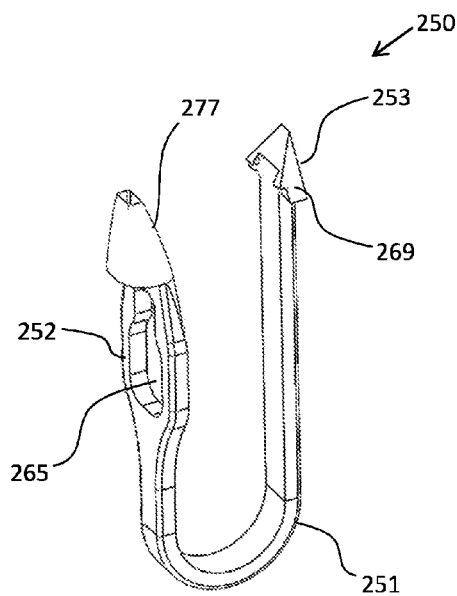
FIGS. 27A-27C depict a pre-formed clip according to certain embodiments.
Figure 27B:
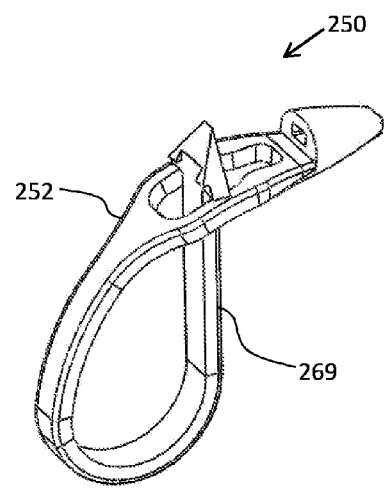
Figure 27C:
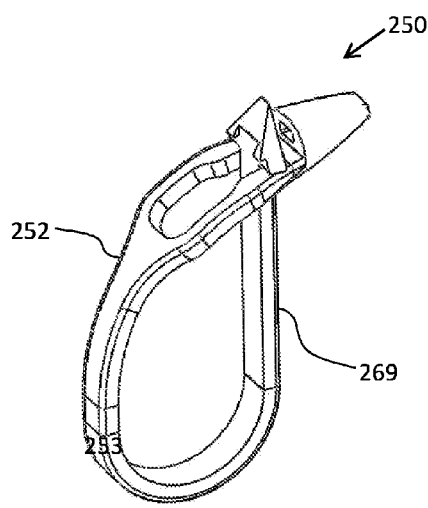
Figure 28:
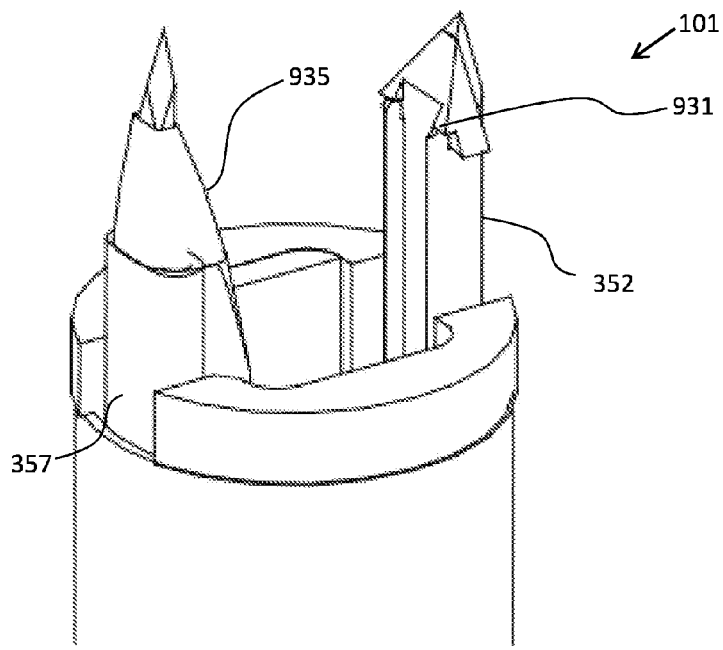
FIGS. 28 and 29 depict a applicator section.
Figure 29:
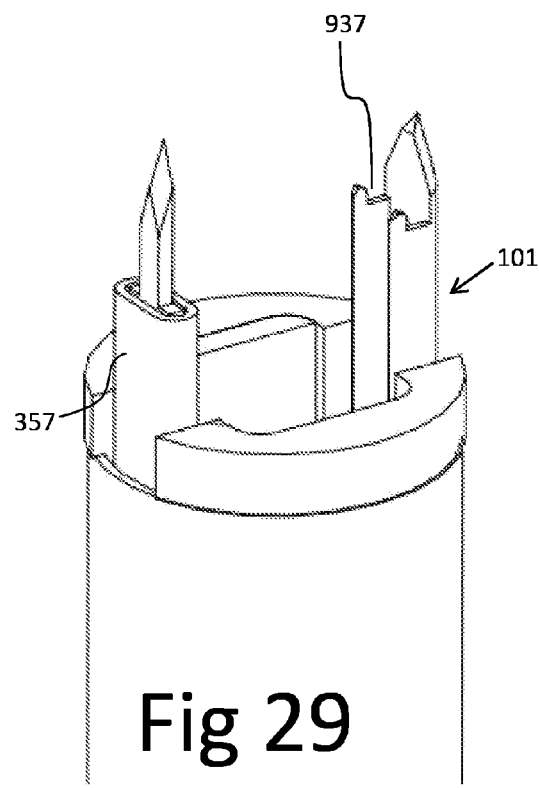

FIGS. 27A-27C depict a clip 250 according to certain embodiments. Preferably, clip 250 is pre-formed to have substantially the shape shown in FIGS. 27A-27C. FIG. 27A shows pre-formed clip 150 in an open configuration, while FIG. 27B shows clip 250 in a closed configuration. FIG. 27C shows clip 250 in a locked configuration. Clip 250 includes insertion slope 277 and at least one barb 269 that are dimensioned to operate with hook insertion needle 352 and loop insertion needle 357 of the embodiment shown in FIGS. 16 and 17. First member 253 includes a hook and second member 252 includes a loop FIG. 28 shows an applicator section of a fastening device with clip 250 according to certain embodiments. FIG. 29 shows the applicator section of FIG. 28, without a clip 250. FIG. 28 shows loop insertion needle 357 and hook insertion needle 352. As shown in FIG. 28, the needle integration section 935 is shaped as a continuation of the needle tip in order to a allow penetration through the mesh and the tissue layers. Specifically, clip 250 includes insertion slope 277 and the applicator includes a sloped needle integration section 935 that are dimensioned to cooperate to provide a substantially smooth, continual slope. Bulges 931 prevent the mesh fibers and the tissue from being caught between clip 250 and hook insertion needle 352. As shown in FIG. 29, slot 937 is operable to hold the hook side of clip 250 in place during penetration, e.g., by engaging barbs 269.

Figure 30A:
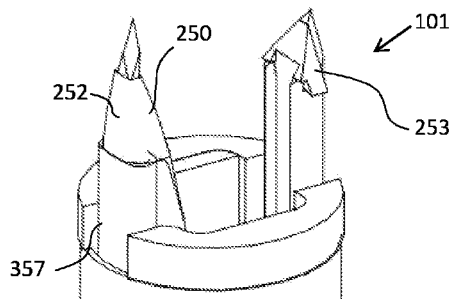
FIGS. 30A-30F depict the operation of a fastening device of certain embodiments.
Figure 30B:
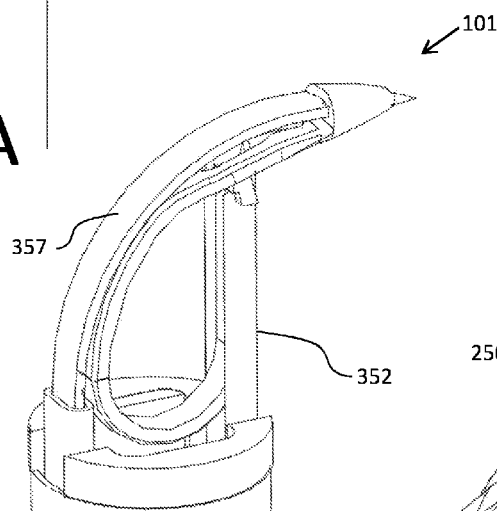
Figure 30C:
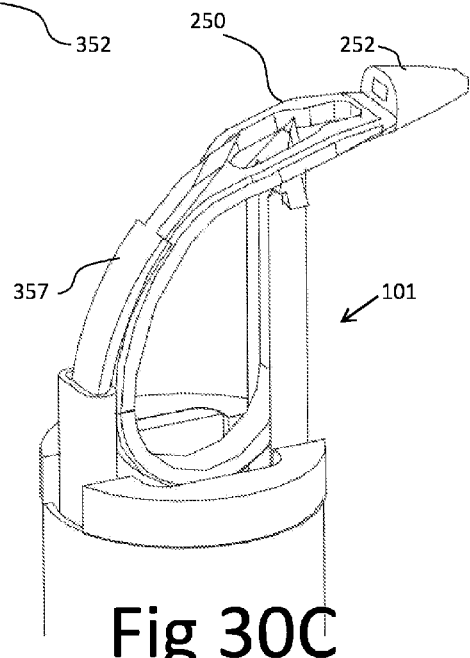

FIGS. 30A-30F depict the operation of applicator section 101 of the applicator section depicted in FIGS. 28 and 29. FIG. 28A shows an initial stage of operation. Hook insertion needle 352 and loop insertion needle 357 are fully engaged with first member 253 and second member 252, respectively, of clip 250. As seen in FIG. 30B, the loop is fully deployed and the hook partially penetrates the loop. In FIG. 30C, hook insertion needle 352 holds the loop in place while the loop insertion needle 357 is retracted.

Figure 30D:
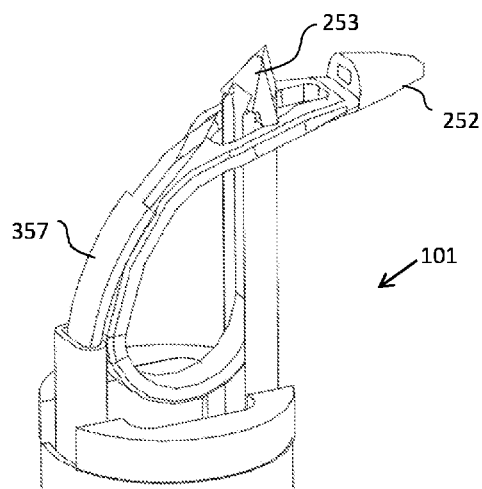
Figure 30E:
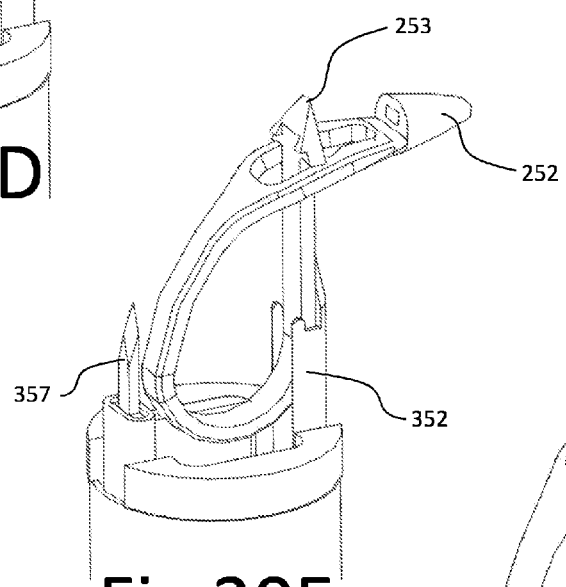
Figure 30F:
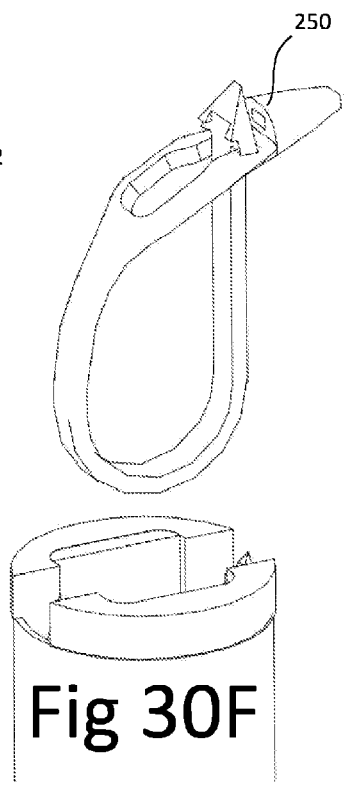

FIGS. 30D-30F show locking and release of clip 250. FIG. 30D shows hook insertion needle 352 pushing the hook through the loop. As shown in FIG. 30E, since the hook is slightly wider than the loop's wide section, first member 253 is caught in second member 252 and removed from the hook insertion needle 352 once hook insertion needle 352 is retracted. FIG. 30F shows that, once tension is applied on the clip, the hook slides to the narrow section of the hook. In this stage the clip is locked.

Figure 31:
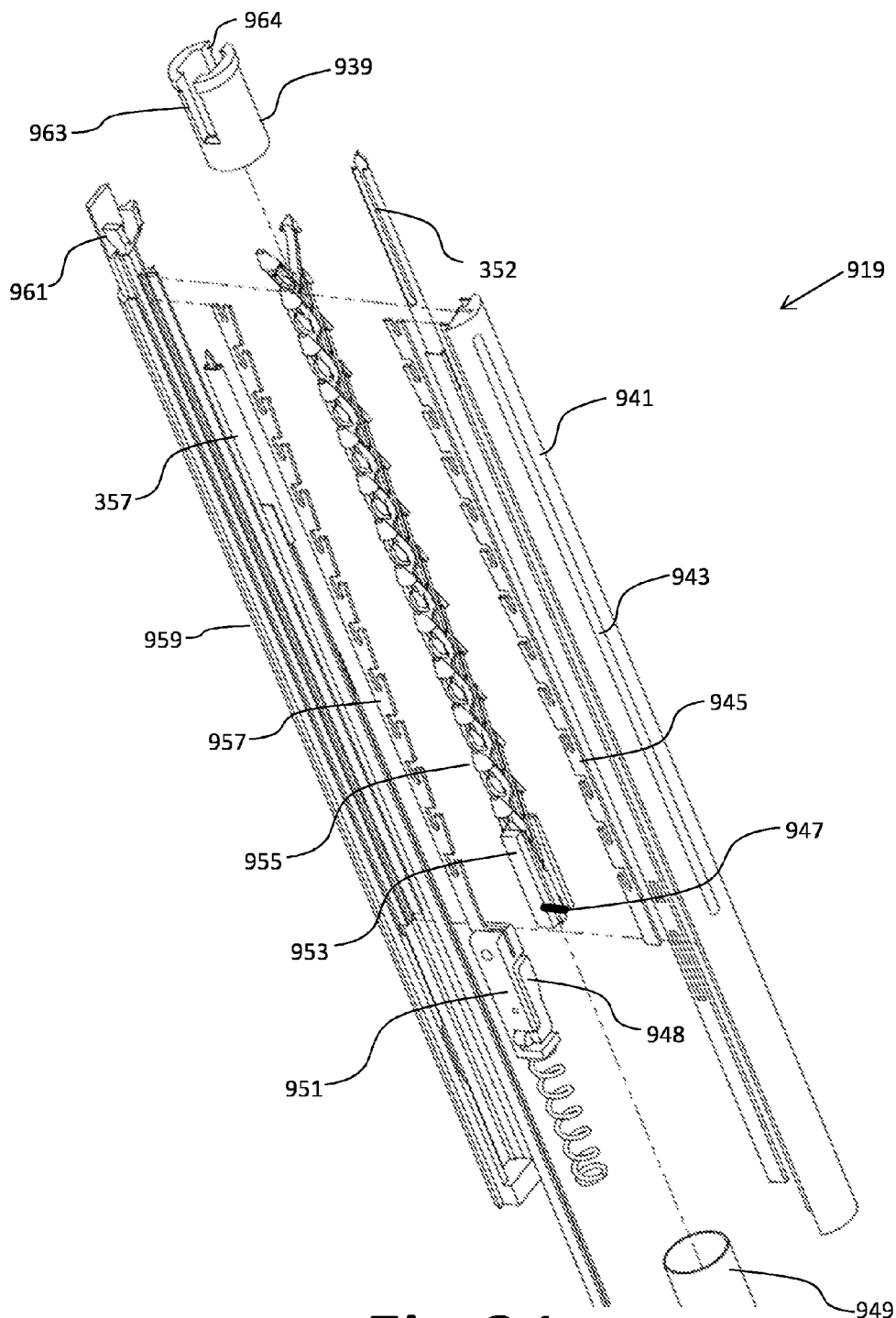
FIG. 31 shows the structure of the clip feeder mechanism.

FIG. 31 shows the structure of the clip feeder 919. FIG. 29 shows hook insertion needle 352 lies under front feeder cover 941, which includes marker slot 943. Front cover 941 covers hold comb 945. Clip stack 955 includes a plurality of clip 250 extending from clip support slide 953, which also includes marker pin 947. Front cover 941 and back cover 959 covering and holding the clip stack 955 and the clip support 953, said front and back cover can be at least partially, substantially, or entirely encapsulated within the shaft cover 949 and terminate at shaft cap 939. Comb driver assembly 951 with comb driver hook 948 operates drive comb 957, as described below. Clip feeder 919 includes loop insertion needle 357 disposed near clip spreader 961. Shaft cap 939 includes a loop collection slot 963 and a hook collection slot 964. Clip feeder 919 functions to deliver one clip 250 from clip stack 955 per operation of device 100.

Figure 32:
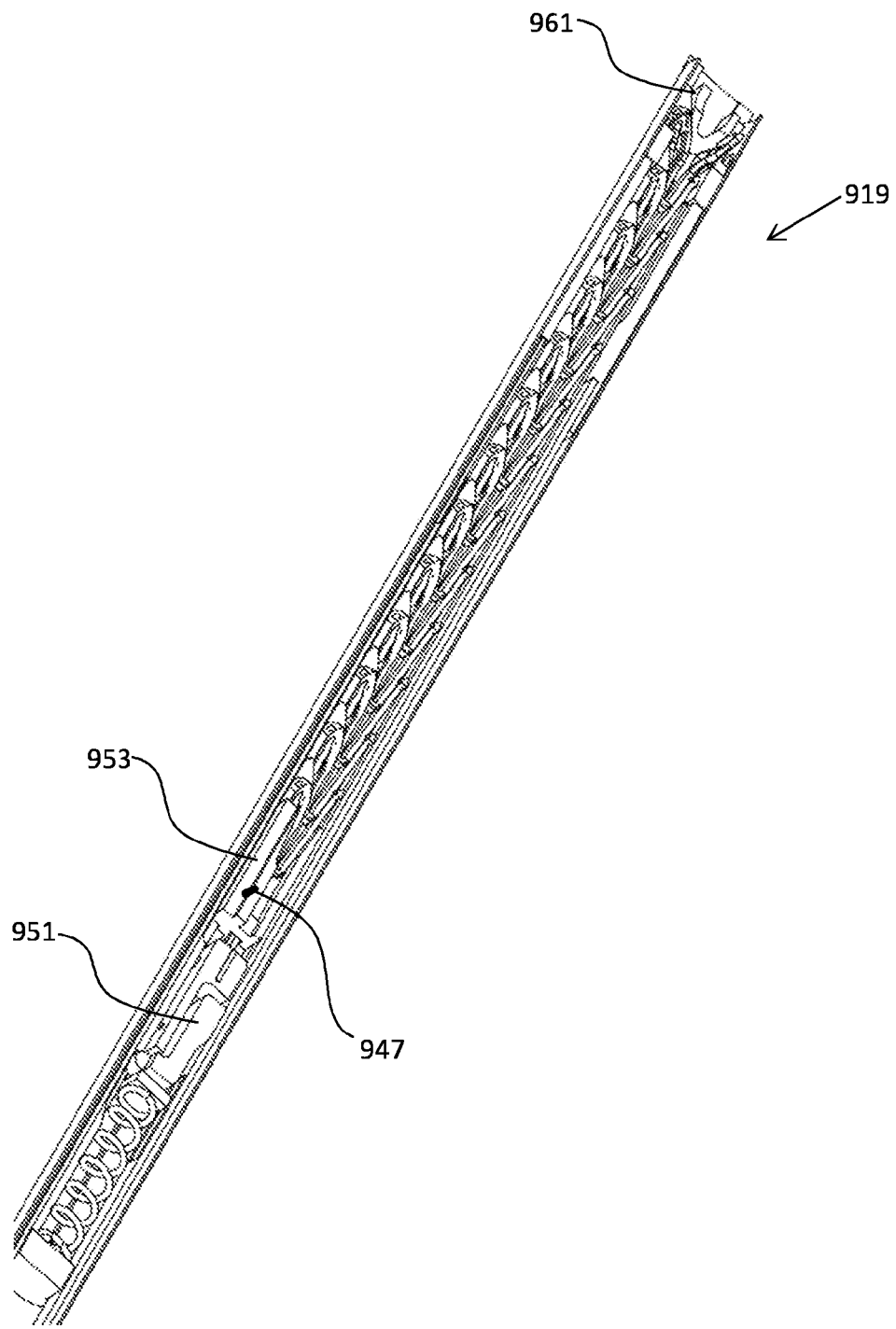
FIG. 32 illustrates the function of the clip feeder.

FIG. 32 illustrates an assembled clip feeder 919. In operation, the comb driver assembly 951 first generates a single up and down stroke of the back drive comb at the end of each application cycle. As a response to the stroke, the entire clip stack 955 is pushed forward by the drive comb 957. During this process the hold comb 945 (not shown) prevents a downward movement of the pre-formed clips 250 in clip stack 955. Once the clips stack 955 is pushed upward (e.g., forward), the last clip 250 is spread by the clip spreader 961 and is positioned at the collection slots 963 and 964, ready to be collected by the insertion needles 352 and 357 during the next application cycle. Each clip 250 supports the next clip 250 and prevents the lateral movement of its middle while it is pushed by drive comb 957. The last clip 250 is supported by the clip support slide 953. Clip support slide 953 is pushed by the drive comb 957 together with the clips. A marker pin 947 may protrudes to the outer surface of the shaft, through the marker slots at the feeder covers 941, to indicate to the surgeon how many clips remains in the device.

Figure 33:
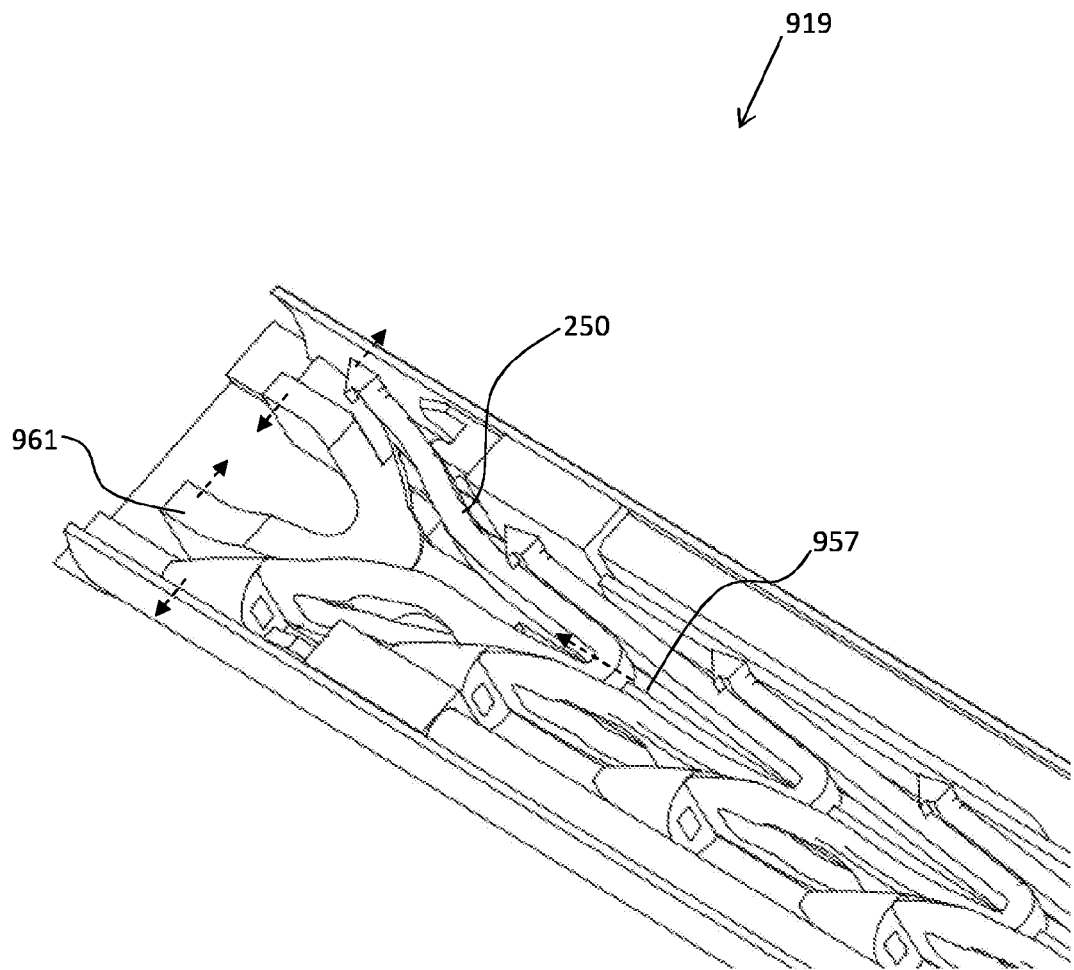
FIG. 33 shows the positioning of a pre-formed clip in a clip feeder.

FIG. 33 shows the positioning of a clip 250 in clip feeder 919. The arms of spreader 961 are flexible and can flex toward the center of the shaft in order to allow the ends of clip 250 to exit from the device. Spreader 961 also provides resistance in order to allow the integration between needle and the clip 250 and hold the last clip 250 in place before its application. The last clip 250 is pushed forward against the spreader 961 by the drive comb 957. As a result, the ends of clip 250 are spread into the collection slots 963 and 964 from which they are collected by the insertion needles during the insertion process. The bottom side of the spreader 961 in sloped in order to allow the extraction of clip 250 once it was collected by the insertion needles.

Figure 34A:
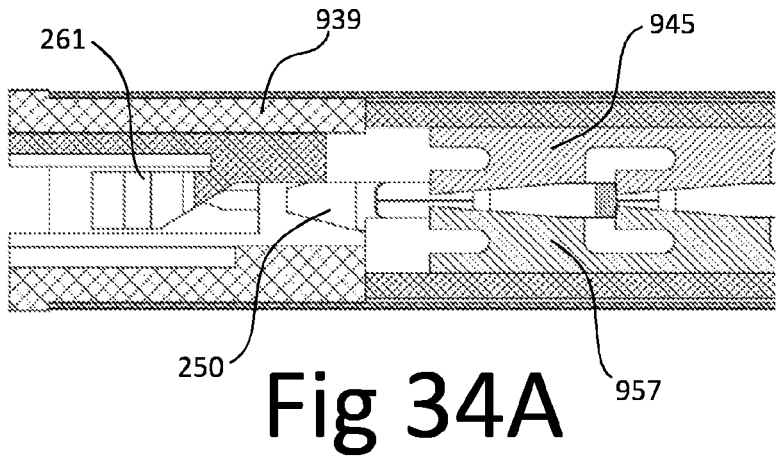
FIGS. 34A-34E show the advancement of a pre-formed clip through the clip feeder.
Figure 34B:
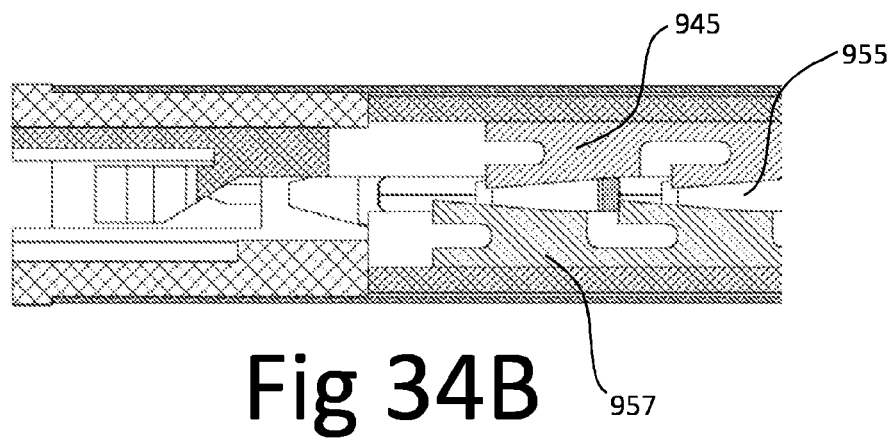
Figure 34C:
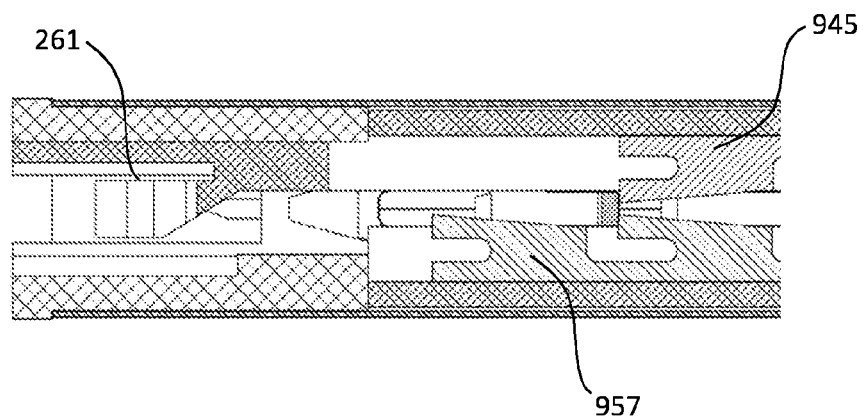

FIGS. 34A-34E show the advancement of a clip 250 through clip feeder 919. FIGS. 34A-34E are cross-sections of a distal end of clip feeder 919 and they depict a loading of a new clip 250 into the collection slots 963 and 964 once a clip 250 is applied. FIG. 34A shows shaft cap 939 in an end of shaft cover 949 with clip spreader 961 therein. In the illustrated embodiment, clip feeder 919 provides a fastener carrier operably connected to cover 949 of shaft 103. In a related embodiment (not illustrated), front cover 941 and back cover 959 provide at least part of an outer surface of the device and are operably connected to a portion of shaft 103 by a suitable means such as adhesive, threading, press-fit, co-molding, heat staking, etc. Also visible is clip 250, being controlled by drive comb 957 and hold comb 945. In an initial stage in FIG. 34A, after the first clip 250 is collected and inserted into the tissue, the next clip 250 is placed below the collection slots 963 and 964. As shown in FIG. 34B, drive comb 957 is moving back while the hold comb 945 is holding the clips stack 955 in place. The teeth of the drive comb 957 are bent while they are climbing over the clip stack 955. FIG. 34C shows drive comb 957 engaged with bottom section of the pre-formed clips in clip stack 955.

Figure 34D:
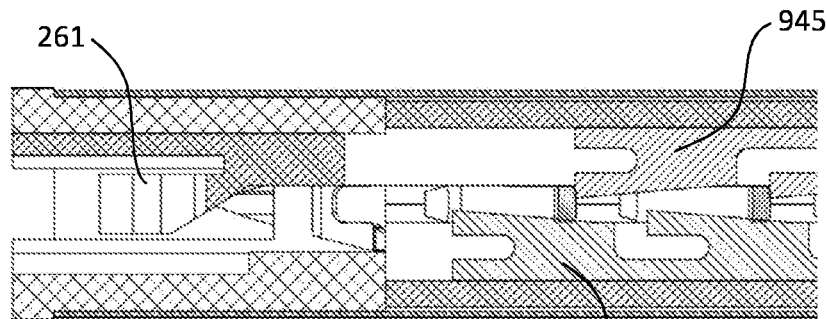
Figure 34E:
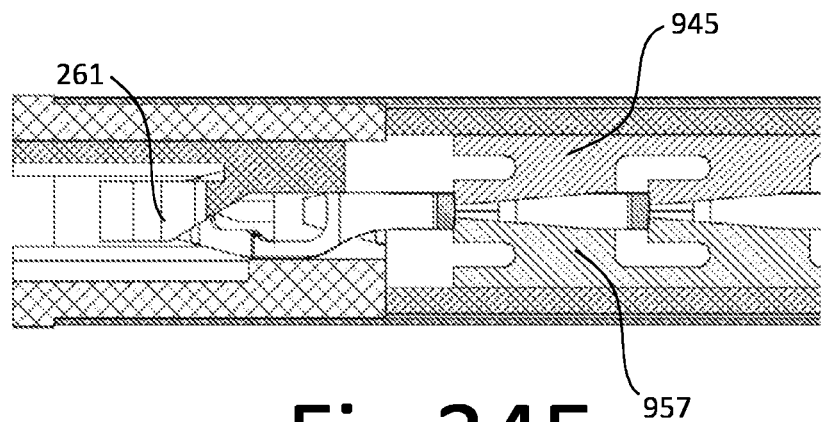

FIG. 34D shows drive comb 957 pushing one of pre-formed clips 250 forward and toward the spreader 961 while climbing over the teeth of the hold comb 945 (which are bent during the process). As seen in FIG. 34E, the next clip 250 is positioned at the collection slots 963 and 964 and is ready to be collected by the insertion needles 352 and 357.

Figure 35A:
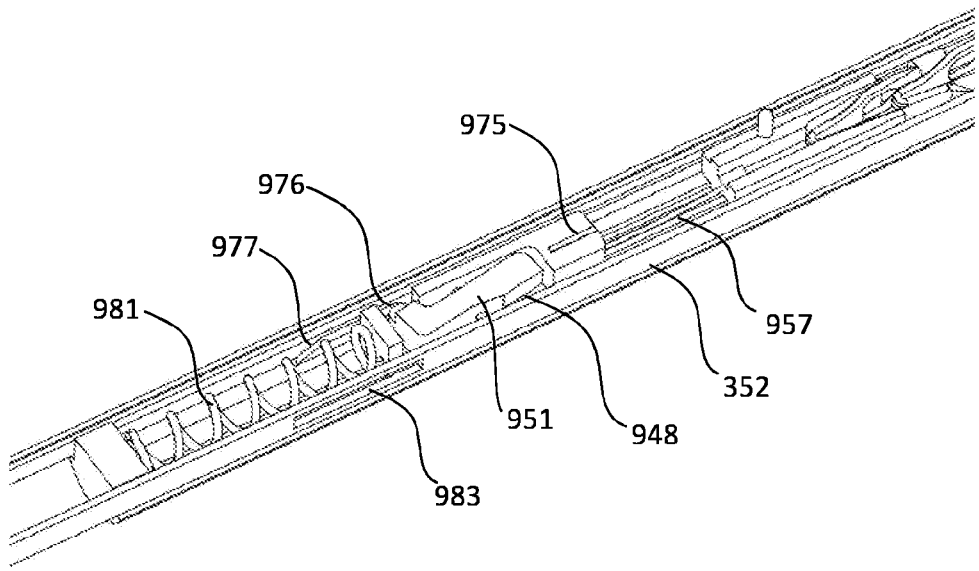
FIGS. 35A-35E depict the operation of the comb driver mechanism of a clip feeder.
Figure 35B:
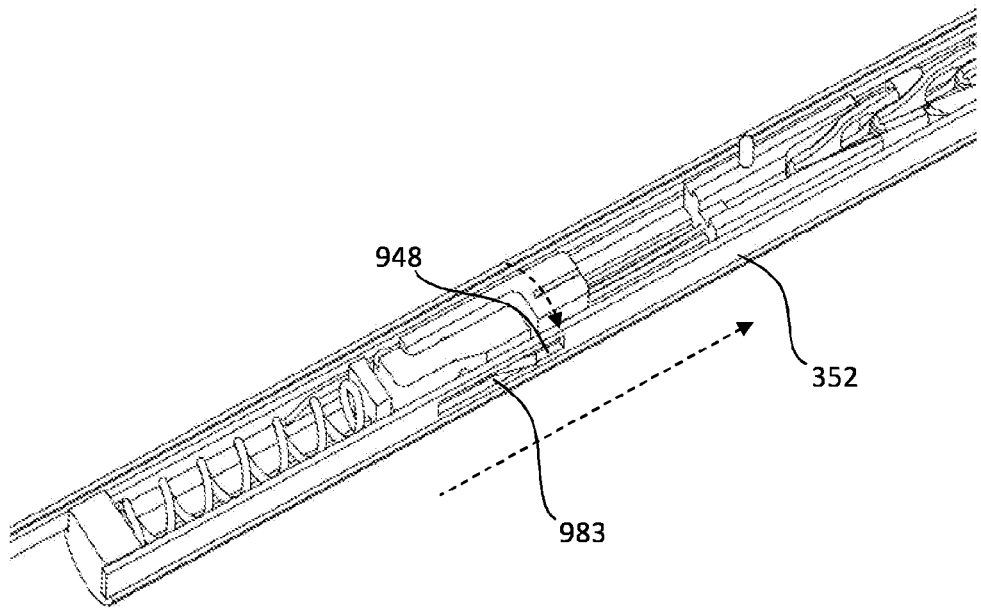

FIGS. 35A-35E depict the operation of the comb driver mechanism of clip feeder 919. As seen in FIG. 35A, comb driver assembly 951 provides a connection between comb driver hook 948 plus comb driver slide 975 and drive comb

957. Release slope 977 and release bulge 976 release the comb driver hook from the hook insertion needle. Comb driver spring 981 can be seen by hook slot 983. The comb driver hook 948 is connected to the comb driver slide 975 by a flexible pin, allowing its rotation. FIG. 33A shows an initial stage, in which hook inserting needle 352 is positioned backward. Hook engagement is depicted in FIG. 33B. Once an application cycle starts, hook insertion needle 352 moves forward. Once the hook slot 983 is positioned in front of the comb driver hook 948, comb driver hook 948 springs into hook slot 983.

Figure 35C:
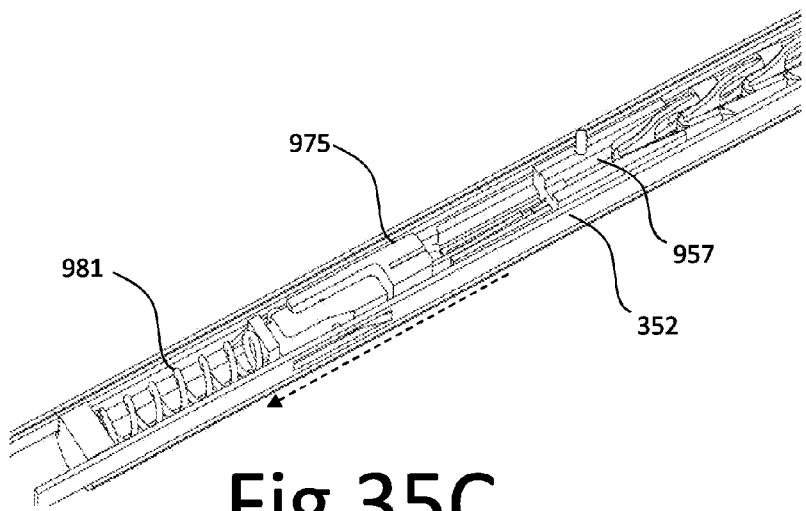
Figure 35D:
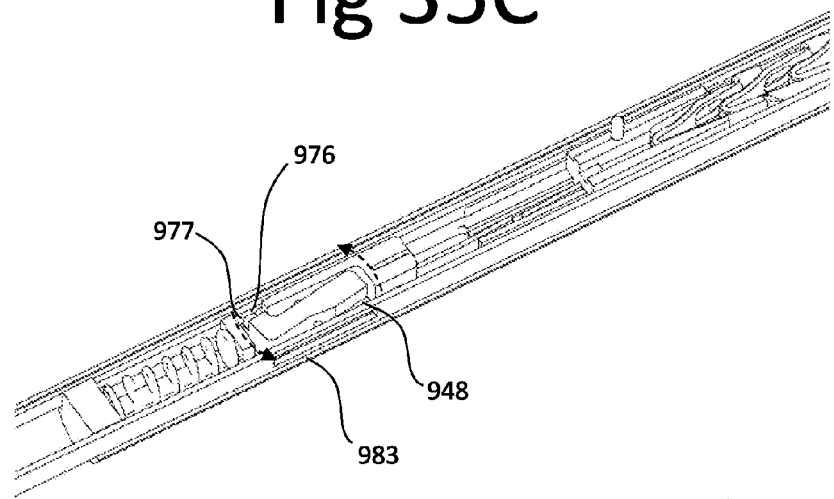
Figure 35E:
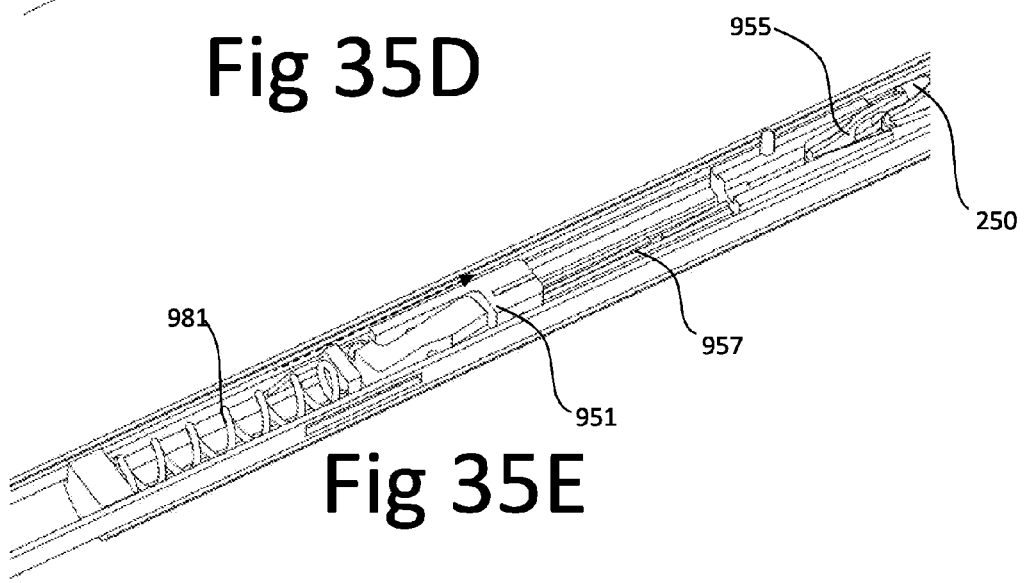

FIG. 35C depicts a pulling back stage. At the final stage of the application cycle, the hook insertion needle 352 moves back while pulling the back the comb driver slide 975 and the drive comb 957 while pressing the comb driver spring 981. During this movement the comb teeth are engaged with pre-formed clips 250. FIG. 35D shows release. Once the release bulge 976 reaches the release slope 977, release bulge 976 is pushed laterally and removes the hook 948 out of the hook slot 983. FIG. 35E shows advancement of clip 250. The compressed spring 981 pushes the comb driver 951 and the drive comb 957 forward while advancing the entire clip stack 955.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A device for delivering a plurality of pre-formed clips, one at a time, into tissue of a patient, the device comprising:
   a handle including a trigger;
   an elongated cylindrical shaft extending distally from the handle along a longitudinal axis, the shaft being longer along the longitudinal axis than the handle and configured to be passed through a trocar in a surgical incision and into an abdomen of the patient;
   an applicator section having a plurality of pre-formed clips of differing sizes disposed therein, each of the plurality of clips formed as a single piece with two terminating ends, one of the two terminating ends of each of the clips including a hook and the other one of the two terminating ends of each of the clips including a loop; and
   first and second elongated members disposed within the applicator section, aligned parallel to the longitudinal axis, independently translatable along the longitudinal axis, and movable out of and into the applicator section to deliver, one at a time and to differing penetration depths, at least a portion of each of the clips out of a distal tip of the applicator section, through a hernia mesh, and into the patient's tissue upon activation of the trigger by an operator of the device when the elongated shaft is inserted through the trocar and into the abdomen,
   the first member configured to engage the hook of a first clip, extend along a straight path parallel to the longitudinal axis to penetrate the patient's tissue, and carry the hook through the patient's tissue when the first member is moved from within the applicator section to out of the applicator section,
   the second member comprising a flexible, pre-shaped portion and configured to engage the loop of the first clip, extend along a straight path parallel to the longitudinal axis and along a curved path to penetrate the patient's tissue, and carry the loop through the patient's tissue when the second member is moved from within the applicator section to out of the applicator section,
   the first and second members configured to fasten the hook to the loop within the patient's tissue when the first and second members are fully extended out of the applicator section, thereby to fasten the plurality of pre-formed clips at differing depths,
   the first and second members also configured to leave the fastened clip within the patient's tissue and to engage the hook and the loop of another one of the plurality of pre-formed clips when the first and second members are retracted back into the applicator section, wherein the device is configured to deliver the pre-formed clips of different sizes to different penetration depths within the patient's tissue.

2. The device of claim 1, wherein the first and second members are configured to penetrate a prosthetic mesh and the patient's tissue.

3. The device of claim 2, further comprising a first push rod that comprises the first member at a distal end of the first push rod, and a second push rod that comprises the second member at a distal end of the second push rod.

4. The device of claim 1, wherein the device further comprises an articulation joint disposed between the shaft and the applicator section, the articulation joint allowing movement of the applicator section off of the longitudinal axis.

5. The device of claim 1, wherein the applicator section is configured to receive a cartridge loaded with the plurality of pre-formed clips.

6. The device of claim 5, wherein the cartridge is from a set of cartridges, at least two of the cartridges in the set carrying clips of a different size.

7. The device of claim 1, wherein each of the hooks is tapered.

8. The device of claim 7, wherein each of the loops comprises an aperture comprising a wide section and a narrow section, the narrow section being distal to the wide section and having a width such that the narrow section retains the terminating end comprising the hook.

9. A device for fastening a mesh over a hernia, the device comprising:
   a handle comprising a trigger;
   an elongated cylindrical shaft extending distally from the handle along a longitudinal axis, the shaft being longer along the longitudinal axis than the handle and dimensioned and configured to be passed through a trocar in a surgical incision and into an abdomen of a patient;
   a fastener carrier operably connected to the shaft;
   first and second elongated insertion needles aligned parallel to the longitudinal axis and extending through at least a portion of the shaft, the second elongated insertion needle comprising a flexible, pre-shaped portion; and a first pre-formed fastener loaded within the fastener carrier, the first pre-formed fastener formed as a first single piece with a first hook end and a first loop end; and a second pre-formed fastener loaded within the fastener carrier, the second pre-formed fastener formed as a second single piece with a second hook end and a second loop end, the first pre-formed fastener and the second pre-formed fastener being of different sizes, and wherein when the carrier is inserted through the trocar and into the abdomen and positioned at tissue and the trigger is squeezed the first and second insertion needles translate independently of each other, the second insertion needle travels a distance from the shaft in a line and assumes a curved conformation a distance away from a terminus of the shaft, pushing the first loop end of the first pre-formed fastener through the tissue, and the first insertion needle travels a distance from the shaft in a line parallel to the longitudinal axis, pushing the first hook end of the first pre-formed fastener through the tissue and bringing the first hook end into contact with the first loop end, wherein the insertion needles thereby:
    push the first hook end and the first loop end of the first pre-formed fastener out of a distal tip of the elongated shaft and through the tissue to a delivery depth corresponding to a physical dimension of the first pre-formed fastener,
    form the first pre-formed fastener into a closed loop beneath the tissue,
    release from the closed-loop fastener, and
    engage the second pre-formed fastener for delivery.

10. The device of claim 9, wherein the second pre-formed fastener has a second dimension and second delivery depth that varies from the physical dimension and the delivery depth of the first pre-formed fastener.

11. The device of claim 9, wherein the fastener carrier is loaded with long, medium, and short fasteners.

12. The device of claim 9, wherein the delivery depth of the first pre-formed fastener is represented by a dimension of the first pre-formed fastener and a delivery depth of the second pre-formed fastener is represented by a dimension of the second pre-formed fastener.

13. The device of claim 9, wherein the device further comprises an articulation joint that allows movement of the fastener carrier off of an axis of the shaft.

* * * * *